US005817308A

United States Patent [19]

Scott et al.

[11] Patent Number: 5,817,308

[45] Date of Patent: Oct. 6, 1998

[54] TOLEROGENIC FUSION PROTEINS OF IMMUNOGLOBULINS AND METHODS FOR INDUCING AND MAINTAINING TOLERANCE

[75] Inventors: David W. Scott, Pittsford; Elias T. Zambidis, Rochester, both of N.Y.

[73] Assignee: University of Rochester, Rochester, N.Y.

[21] Appl. No.: 195,874

[22] Filed: Feb. 11, 1994

[51] Int. Cl.[6] .......................... A01N 63/00; A61K 39/35; C12N 5/10

[52] U.S. Cl. .................................... 424/93.21; 435/320.1; 435/172.3; 435/325; 435/326; 435/328; 435/91.31; 530/387.3; 514/44; 536/22.1; 536/23.1; 424/130.1; 424/184.1; 424/133.1; 424/185.1

[58] Field of Search ....................... 514/2, 44; 424/93.21, 424/130.1, 184.1, 133.1, 185.1; 435/320.1, 172.3, 91.31, 325, 326, 328, 349–373; 536/22.1, 23.1; 530/387.3

[56] References Cited

U.S. PATENT DOCUMENTS 5,167,956 12/1992 Neville et al. .

FOREIGN PATENT DOCUMENTS

WO 90/09804 9/1990 European Pat. Off. .
WO 92/06193 4/1992 European Pat. Off. .
WO9009804 9/1990 WIPO .

OTHER PUBLICATIONS

Ballard et al., "Mutational analysis of the immunoglobulin heavy chain promoter region," *PNAS USA*, 83, 9626 (1986).

Barbas et al., "Assembly of combinatorial antibody libraries on phage surfaces: The gene III site," *PNAS USA*, 88, 7978 (1991).

Bond et al., "Multiple *Amb a* I Allergens Demonstrate Specific Reactivity With IgE and T Cells From Ragweed–Allergic Patients," *J. Immunol.*, 146, 3380 (1991).

Borel, "Haptens Bound to Self IgG Induce Immunologic Tolerance, White When Coupled to Syngeneic Spleen Cells They Induce Immune Suppression," *Immunological Reviews*, 50, 71 (1980).

Chambers et al., "Ectopic lymphokine gene expression in human peripheral blood lymphocytes in vivo," *PNAS USA*, 89, 1026 (1992).

"Partial Digestion of DNA with Restriction Endonucleases," in *Current Protocols in Molecular Biology*; Ausubel et al., eds.; J. Wiley & Sons: New York, NY; vol. 1: Supplement 3.1.3; (1987).

"Enzymatic Manipulation of DNA and RNA" in *Current Protocols in Molecular Biology*; Ausubel et al., eds.; J. Wiley/Greene Publishing Associates: New York, NY; Chapter 3, pp. 3–1 to 3–44; (1992).

Gauer et al., "B Cell Tolerance Induction by Cross–Linking Membrane IgM, but not IgD, and Synergy by Cross–Linking of Both Isotypes," *Journal of Immunology*, 150, 1663 (1993).

Hebell et al., "Suppression of the Immune Response by a Soluble Complement Receptor of B Lymphocytes," *Science*, 254, 102 (1991).

Huse et al., "Generation of a Large Combinatorial Library of the Immunoglobulin Repertoire in Phage Lambda," *Science*, 246, 1275 (1989).

Jennings et al., "Fimbage of *Bacteriodes nodosus*: protein engineering of the structural subunit for the production of an exogenous peptide," *Protein Eng.*, 2, 365 (1989).

Kang et al., "Long–term expression of a T–cell receptor β–chain gene in mice reconstituted with retrovirus–infected hematopoietic stem cells," *PNAS USA*, 87, 9803 (1990).

Kuo et al., "Purification and Immunochemical Characterization of Recombinant and Native Ragweed Allergen *Amb a* II," *Molecular Immunol.*, 30, 1077 (1993).

Lai et al., "T Cell Receptor Gene Usage in the Response to λ Repressor cI Protein, An Apparent Bias in the Usage of a Vα gene Element," *J. Exp. Med.*, 168, 1081 (1988).

Lanza et al., "Use of Antigenized Antibodies Containing CD4 Sequences to Generate Antibodies Able to Inhibit Syncytia Formation," *FASEB Journal*, 6, A1400, Abstract No. 2690 (1992).

Olson et al., "Two Major Human Allergenic Sites on Ragweed Pollen Allergen Antigen E Identified By Using Monoclonal Antibodies," *J. Immunol.*, 136, 2109 (1986).

Rafnar et al., "Cloning of *Amb a* I (Antigen E), the Major Allergen Family of Short Ragweed Pollen," *J. Biol. Chem.*, 266, 1229 (1991).

F. Ria et al., "Immunological activity of covalently linked T–cell epitopes," *Nature*, 343, 381 (1990).

Rossi et al., "Adhesive Functions of Antibodies Antigenized with the Arg Gly Asp (RGD) Epitope," *FASEB Journal*, 6, A1400, Abstract No. 2691 (1992).

Rutgers et al., "Hepatitis B Surface Antigen as Carrier Matrix for the Repetitive Epitope of the Circumsporozoite Protein of *Plasmodium Falciparum*," *Biotechnology*, 6, 1065 (1988).

Scherer et al., "Control of Cellular and Humoral Immune Responses by Peptides Containing T–Cell Epitopes," in *Symp. on Quant. Biol.*; Cold Spring Harbor: New York, NY; vol. 54; pp. 497–504 (1989).

(List continued on next page.)

*Primary Examiner*—Christopher S. F. Low
*Attorney, Agent, or Firm*—Morrison & Foerster

[57] ABSTRACT

The invention provides methods and compositions for inducing and maintaining tolerance to epitopes or antigens containing the epitopes. The compositions include expression cassettes and vectors including DNA sequences coding for a fusion immunoglobulin operably linked to transcriptional and translational control regions functional in a hemopoietic or lymphoid cell. The fusion immunoglobulin includes at least one heterologous tolerogenic epitope at the N-terminus variable region of the immunoglobulin. Cells stably transformed with the expression vector are formed and used to produce fusion immunoglobulin. The invention also provides methods for screening for novel tolerogenic epitopes and for inducing and maintaining tolerance. The methods of the invention are useful in the diagnosis and treatment of autoimmune or allergic immune responses.

28 Claims, 9 Drawing Sheets

OTHER PUBLICATIONS

Scott, "Cellular Events in Tolerance—V. Detection, Isolation and Fate of Lymphoid Cells Which Bind Fluoresceinated Antigen in–Vivo," *Cell. Immunol.,* 22, 311 (1976).

Scott, "Multiple Pathways of B Lymphocyte Tolerance," *Immunol. Rev.,* 43, 241 (1979).

Smith, "Immunological Tolerance of Nonliving Antigens," *Advances in Immunology*, 1, 67 (1961).

Warner et al., "A Polyclonal Model for B Cell Tolerance—I. Fc–Dependent Induction of Nonresponsiveness by Pretreatment of Normal Splenic B Cells with Anti–Ig," *J. Immunol.,* 146, 2185 (1991).

Zanetti et al., "Antigenized Antibodies," *Nature*, 355, 476 (1992).

Venkataraman, M., et al., "Persistence of Antigen–Binding Cells with Surface Toleragen: Isologous Versus Heterologous Immunoglobulin Carriers", *J. immunol.,* 119, 1006–1009 (1977).

Chambers et al., PNAS USA, 89:1026–1030, 1992.

Ria et al., Nature, 343:381–383, 1990.

Zambidis et al., J. Cell Biochem., 17B, 1993, 251 FZ434.

NIH "Report and Recommendations . . . ", Dec. 7, 1995, 1–40.

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
( A ) LENGTH: 45 base pairs

-continued ( B ) TYPE: nucleic acid
( C ) STRANDEDNESS: double
( D ) TOPOLOGY: linear ( i i ) MOLECULE TYPE: DNA ( x i ) SEQUENCE DESCRIPTION: SEQ ID NO:1:

CTGGAGGACG CGCGGCGGCT GAAGGCGATA TACGAGAAGA AGAAG 45

( 2 ) INFORMATION FOR SEQ ID NO:2:

( i ) SEQUENCE CHARACTERISTICS:
( A ) LENGTH: 15 amino acids
( B ) TYPE: amino acid
( C ) STRANDEDNESS: unknown
( D ) TOPOLOGY: linear ( i i ) MOLECULE TYPE: peptide ( x i ) SEQUENCE DESCRIPTION: SEQ ID NO:2:

Leu Glu Asp Ala Arg Arg Leu Lys Ala Ile Tyr Glu Lys Lys Lys
1 5 10 15

( 2 ) INFORMATION FOR SEQ ID NO:3:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:3:

TGATCTACTG CAGCTGGAGG ACGCGCGGCG G 31

( 2 ) INFORMATION FOR SEQ ID NO:4:

( i ) SEQUENCE CHARACTERISTICS:
( A ) LENGTH: 40 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:4:

CGACCTCCTG CAGTTGGACC TGCTTCTTCT TCTCGTATAT 40

( 2 ) INFORMATION FOR SEQ ID NO:5:

( i ) SEQUENCE CHARACTERISTICS:
( A ) LENGTH: 75 base pairs
( B ) TYPE: nucleic acid
( C ) STRANDEDNESS: single
( D ) TOPOLOGY: linear ( i i ) MOLECULE TYPE: DNA ( i x ) FEATURE:
( A ) NAME/KEY: CDS
( B ) LOCATION: 16..61

( x i ) SEQUENCE DESCRIPTION: SEQ ID NO:5:

CAGGTCCAAC TGCAG CTG GAG GAC GCG CGG CGG CTG AAG GCG ATA TAC GAG 51
Leu Glu Asp Ala Arg Arg Leu Lys Ala Ile Tyr Glu
1 5 10

AAG AAG AAG C AGGTCCAACT GCAG 75
Lys Lys Lys
15

-continued ( 2 ) INFORMATION FOR SEQ ID NO:6:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:6:

TGGACTAAGT CGACACCATG GGATGCAGC 29

( 2 ) INFORMATION FOR SEQ ID NO:7:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:7:

GGCAACAGAA GCTTTCACTT CTTCTTCTCG TAT 33

( 2 ) INFORMATION FOR SEQ ID NO:8:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:8:

TGATCTACTG CAGCTGGAGG ACGCGCGGCG G 31

TOLEROGENIC FUSION PROTEINS OF IMMUNOGLOBULINS AND METHODS FOR INDUCING AND MAINTAINING TOLERANCE

This invention was made with Government support under grant No. AI29691 awarded by the National Institutes of Health. The Government has certain rights in the invention.

BACKGROUND OF THE INVENTION

Self-nonself discrimination is one of the cornerstones of immunology. Normally, individuals develop tolerance to self constituents during the early development of the immune system. However, the maintenance of this unresponsive state requires the persistence of antigen, a fact which implies that tolerance induction is a lifelong process. Smith, *Advances in Immunology*, 1:67 (1961). Indeed, the breakdown of tolerance in older individuals explains the increased incidence of autoimmunity in aging populations.

Isologous or heterologous gamma globulins have been used as tolerogenic carrier molecules (primarily IgG's). Scott, *Immunol. Rev.*, 43:241 (1979). Although different sources of IgG's may vary in their persistence and/or mechanism of tolerance induction, by far, IgG carriers have been the most efficacious at tolerance induction in adults to haptens, nucleosides and peptides. Borel, *Immunological Reviews*, 50:71 (1980); and Scott, *Cell Immunol.*, 22:311 (1976). These carriers owe their superior tolerogenicity to their persistence in vivo and the ability of epitopes chemically attached to IgG's to crosslink mIgM with B-cell Fc receptors. However, chemical crosslinking of epitopes to IgG carriers is limited by the availability of free amino groups and the uncontrolled targeting of the added determinant to different portions of the IgG.

Recombinant DNA technology can be used to genetically engineer molecules having heterologous epitopes. For example, heterologous oligopeptide epitopes of biological interest have been expressed in bacterial flagellin (Jennings et al., *Protein Eng.*, 2:365 (1989)); hepatitis B surface antigen (Rutgers et al., *Biotechnology*, 6:1065 (1988)); and in the complementarity determining regions of immunoglobulins (Zanetti et al., *Nature*, 355:476 (1992). Some attempts have been made to test the ability of recombinant proteins to serve as antigens to immunize animals and generate immune responses to the heterologous oligopeptide. However, induction and maintenance of tolerance to oligopeptides presented to the immune system has not been demonstrated. The ability to maintain tolerance to an antigen or epitope requires persistence of the epitope in vivo.

Therefore, there is a need to develop a method of inducing stable and long lasting tolerance to an epitope. There is a need to develop a vector that can provide for persistence of the epitope in vivo so that tolerance is maintained. There is a need to develop a recombinant vector which codes for a recombinant polypeptide that has a heterologous epitope and that can be used to induce and maintain tolerance in individuals.

SUMMARY OF THE INVENTION

The invention provides for methods and compositions for inducing and maintaining tolerance to epitopes and antigens containing those epitopes. The methods and compositions are useful to identify novel tolerogenic epitopes or antigens containing such epitopes. The methods and composition are also useful for inducing and maintaining tolerance to epitopes or antigens containing the epitopes associated with autoimmune or allergic immune responses.

The compositions include an expression cassette and a vector. The expression cassette and vector can be used to form transformed cells. The expression cassette comprises a DNA sequence coding for a fusion immunoglobulin operably linked to transcriptional and translational control regions functional in a hemopoietic or lymphoid cell. The fusion immunoglobulin has at least one heterologous tolerogenic epitope at the N-terminus variable region of the immunoglobulin molecule. A vector includes the expression cassette and is a vector that can provide for stable maintenance, i.e. provide for gene expression of the expression cassette, in the hemopoietic or lymphoid cell throughout the lifetime of the cell. Hemopoietic or lymphoid cells are stably transformed with a vector to provide transformed cells expressing the fusion immunoglobulin.

The invention also includes pharmaceutical compositions. A pharmaceutical composition comprises an amount of a fusion immunoglobulin sufficient to induce and/or maintain tolerance combined with a pharmaceutically acceptable excipient. The fusion immunoglobulin includes at least one heterologous tolerogenic epitope at the N-terminus variable region of the immunoglobulin.

The invention also provides methods for identifying epitopes or antigens containing epitopes that can serve as novel tolerogens. The methods involve stably transforming cells with an expression cassette coding for a fusion immunoglobulin to form a population of transformed cells producing or expressing the fusion immunoglobulin. The fusion immunoglobulin having one or more than one epitope from an antigen suspected of being capable of inducing tolerance can be screened for the ability to induce tolerance to the epitope in a variety of ways. One method of determining whether the fusion immunoglobulin can induce tolerance is to administer a tolerogenic amount of the fusion immunoglobulin to an animal. In another method, the transformed cells expressing the fusion immunoglobulin can be administered to an animal to determine whether tolerance to the epitope can be induced and/or maintained. In a third method, epitopes or antigens containing the epitope can be identified by reactivity with allergic or autoimmune immune serum or lymphocytes.

The invention also includes methods of inducing and maintaining tolerance to an epitope in an animal. One of the methods involves administering a tolerogenic amount of a fusion immunoglobulin sufficient to induce and/or maintain tolerance to the heterologous epitope on the fusion immunoglobulin. In another method, transformed cells expressing a fusion immunoglobulin are administered to an animal to induce and maintain tolerance. In another method, a pharmaceutical composition including a fusion immunoglobulin is administered to induce tolerance to the heterologous epitope and transformed cells expressing the fusion immunoglobulin are then administered to maintain tolerance to the heterologous epitope.

DETAILED DESCRIPTION OF THE INVENTION

Figure 1A:
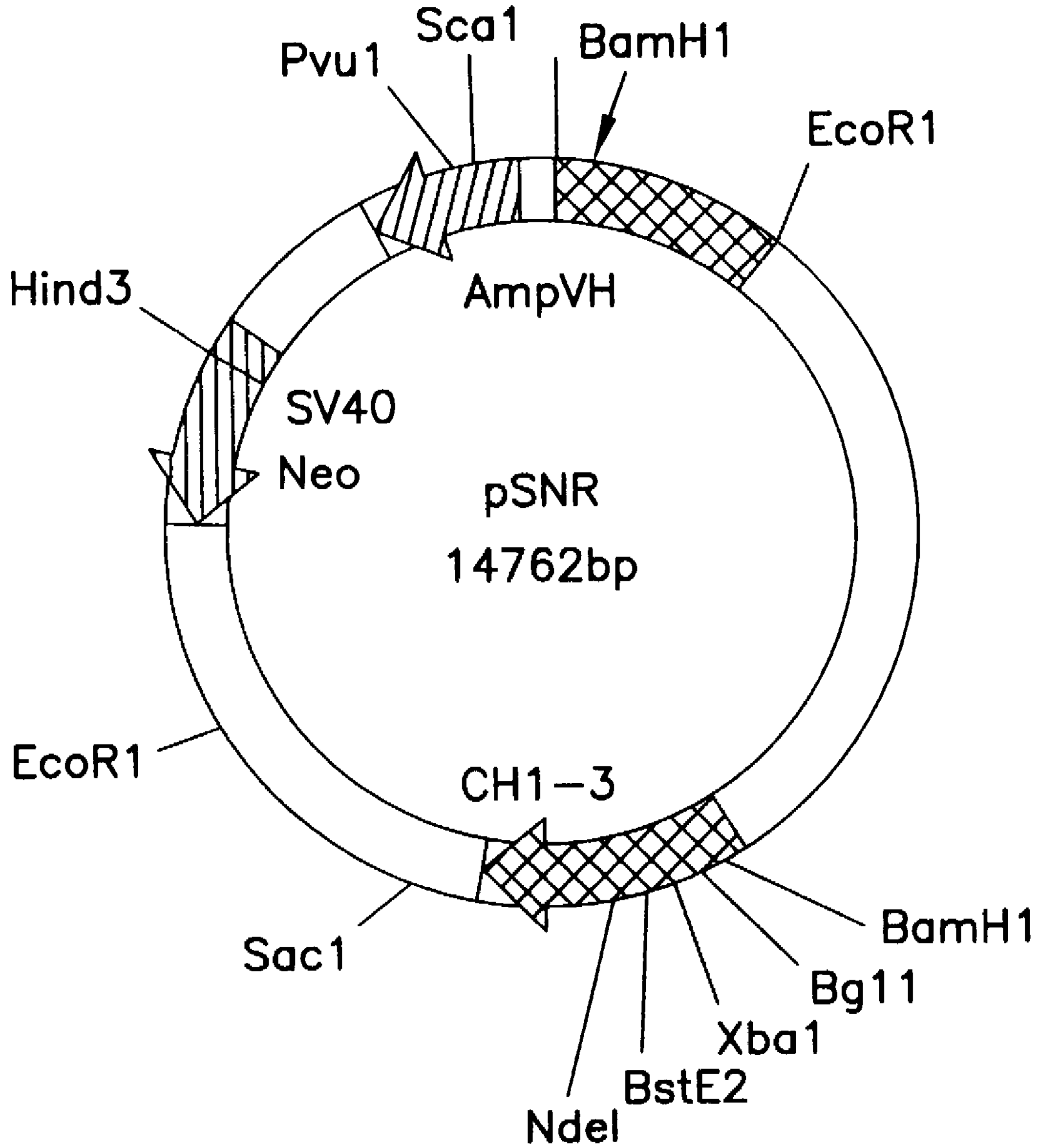
FIGS. 1A and 1B show the strategy for preparation of a murine DNA construct coding for a fusion immunoglobulin including the 12-26 epitope of λ-CI repressor protein at the N-terminus of IgG1: (A) A map of plasmid PSNR containing the genomic sequence for a γ1 H chain, modified as described in Example 1. (B) Restriction map and sequence showing the DNA sequence coding for the 12-26 epitope as combined with the DNA sequence coding for the variable region of the heavy chain.

The invention provides for compositions and methods for inducing and maintaining tolerance to antigens. The compositions include an expression cassette and vector comprising a DNA sequence that codes for a fusion immunoglobulin operably linked to transcriptional and translational control regions functional in a hemopoietic cell or lymphoid cell. The fusion immunoglobulin has at least one heterologous epitope located at the N-terminus of the variable region of the immunoglobulin chain. The vectors are preferably those vectors that can provide for stable integration of the expression cassette into a hemopoietic cell. The invention also includes cells transformed with the vectors. Fusion immunoglobulins having a heterologous epitope at the N-terminus can be used in a pharmaceutical composition that provides for induction of tolerance to the epitope and/or its antigen. The invention also provides for methods of identifying novel tolerogenic antigens and epitopes, as well as methods for inducing and maintaining tolerance to an antigen.

As used herein, the term "antigen" refers to an agent that is capable of eliciting an immune response in an animal.

An "epitope" is a portion of the antigen that is capable of eliciting an immune response and combines with an antibody specific for that portion of the antigen.

A "heterologous epitope" is an epitope that is not normally associated with the immunoglobulin carrier molecule. It is obtained or derived from an antigen that is not the same as the immunoglobulin carrier molecule.

A "hemopoietic cell" is a cell that can form blood cells include lymphocytes and macrophages from such tissues as bone marrow cells and other extramedullary tissues.

An "expression cassette or vector" is stably maintained in a hemopoietic or other cell type when it is either integrated into the chromosome so that the expression cassette or vector is replicated and transmitted to progeny cells or is maintained in the cell without loss of functional activity, i.e. gene expression, over the lifetime of the cell.

A "tolerogenic epitope" is an epitope that can induce immunological unresponsiveness to the epitope and/or an antigen containing an epitope. A tolerogenic epitope is selected because of a desire to induce immunological unresponsiveness to the epitope and/or an antigen containing the epitope. A tolerogenic epitope can be identified as an epitope that can stimulate an immune response if appropriately presented to the immune system or it can be an auto- or self-antigen which may not normally elicit an immune response. A tolerogenic epitope can interact with T cells or B cells or both. Suitable tolerogenic epitopes that can be selected for are preferably those epitopes and/or antigens associated with autoimmune disease or allergic reactions.

A. Expression Cassettes and Vectors

An expression cassette of the invention includes a DNA sequence encoding a fusion immunoglobulin operably linked to transcriptional and translational control regions functional in a hemopoietic or lymphoid cell. The fusion immunoglobulin includes at least one heterologous tolerogenic epitope at the N-terminus variable region. The expression cassette is preferably incorporated into a vector that provides for stable maintenance and expression of the expression cassette in the host cell. If the host cell is a hemopoietic cell, the vector is preferably a vector that provides for integration of the vector into the chromosome of the hemopoietic cell. If the host cell is a lymphoid cell line, the vector can be a non-integrated vector such as a plasmid as long as it provides for stable maintenance and expression of the expression cassette over the lifetime of the cell. The expression cassettes and vectors of the invention are useful to provide fusion immunoglobulins to use as tolerogenic agents and/or to provide for maintenance of tolerance to an antigen and/or epitope.

A DNA sequence encoding a fusion immunoglobulin can be obtained and constructed using standard methods as described in *Current Protocols in Molecular Biology*, Chapter 3, J. Wiley/Greene Press (1992). DNA sequences encoding immunoglobulins can be obtained using known methods such as described by Hebell et al., *Science*, 254:102 (1991) and Huse et al., *Science*, 246:1275 (1989). Briefly, heavy and light chain sequences can be obtained by using reverse transcriptase polymerase chain reaction (RT-PCR) of messenger RNA (mRNA) isolated from spleen cells or, preferably, hybridomas producing an antibody of known specificity. The primers can be designed to amplify the variable light and heavy chain sequences including the Fd fragment ($V_H$-CH1). Examples of such primers are disclosed in Huse et al, cited supra. and Ballard et al., *PNAS*, 83:9626 (1986). Typically such primers are designed to include restriction enzyme recognition sequences at both ends of the sequence to be amplified. The restriction endonuclease recognition sequences are known to those of skill in the art and can be selected to provide for ease of cloning into a vector at a specific location.

The DNA sequences encoding the immunoglobulin's light and heavy chains are preferably cDNA sequences so that any intervening sequence DNA has been removed and a fully functional immunoglobulin is encoded by the DNA sequence. The DNA sequence encoding the immunoglobulin molecule can encode a complete immunoglobulin having both heavy and light chains with the Fc fragment or it can encode portions of the immunoglobulin such as Fab fragment, $F(ab)_2$ fragment, or just the heavy chain. Modifications to the DNA sequence coding for the heavy chain can be made and still result in a fusion immunoglobulin molecule when the DNA sequence coding for the heavy chain is expressed in a cell of B cell lineage that can supply light chains to form the immunoglobulin. The DNA sequence can code for a secreted or membrane form of the immunoglobulin molecule.

Suitable examples of a DNA sequence coding for the heavy chain of an antibody specific for nitrophenyl are described by Hebell et al., cited supra. IgG1 or IgG2 (mouse) are preferred as carrier molecules for inducing tolerance. The DNA sequence preferably codes for the heavy chain of IgG1 or IgG2 types of immunoglobulin.

A DNA sequence coding for at least one tolerogenic epitope of an antigen can be obtained and prepared by standard methods. If the epitope is a small peptide of 15–20 amino acids, the nucleotide sequence encoding that epitope can be synthesized using automated DNA synthesis. If the DNA sequence codes for all or a portion of an antigen (i.e., codes for multiple epitopes), the DNA sequence coding for that antigen can be isolated and subcloned using published methods. The DNA sequences coding for all or a portion of some antigens can also be identified by searching in a database such as GenBank. Once the sequence is identified in such a database or by reference to publications, the DNA sequence coding for all or a portion of an antigen can be obtained by automated synthesis or by polymerase chain reaction (PCR). For example, the DNA sequence coding for antigen E of ragweed pollen has been disclosed by Rafner et al., *J. Biol. Chem.*, 266:1229 (1991); and Kuo et al., *Molecular Immunol.*, 30:1077 (1993). Epitopes of antigen E have also been identified as described by Olson, *J. Immunol.*, 136:2109 (1986); and Bond et al., *J. Immunol.*, 146:3380 (1991). A DNA sequence encoding one or more of the epitopes of antigen E can be obtained by standard methods as described in Kuo et al., cited supra.

Suitable antigens are those that it would be desirable to induce and maintain immunological unresponsiveness to the epitope and/or antigen containing the epitope. Such antigens include pollen, ragweed, dustmites, and other known allergens. Suitable antigens also include autoantigens such as clotting factor VIII, acetylcholine receptors, collagen, myelin basic protein, thyroglobulin, and histocompatibility antigens. A suitable antigen also includes the epitopes from the λ-CI repressor protein. The amino acid sequences of many of these antigens as well as epitopes of these antigens are known to those of skill in the art. The preferred antigens include antigen E of ragweed and clotting factor VIII. The DNA sequences encoding suitable antigens can be obtained and prepared as described herein and in accord with published methods.

Before a DNA sequence coding for at least one tolerogenic epitope of an antigen is obtained and prepared, the epitope and/or antigen is selected. The epitope and/or antigen can be a single epitope or it can be all or a portion of an antigen containing many epitopes. The epitope can be one that interacts with T cells, or one that interacts with B cells, or one that interacts with both T and/or B cells.

The selection of the epitope and/or epitopes can be made based on the following criteria. Epitopes are first selected for the ability to induce tolerance to the peptide or an antigen containing the epitope, preferably an antigen associated with an allergic response or autoimmune response. Secondly, if tolerance is desired to a large and complex antigen, more than one epitope can be selected to be combined into a fusion immunoglobulin. Preferably, the entire antigen may be included in the fusion immunoglobulin. Thirdly, epitopes may be selected if B and/or T cell tolerance is desired. Certain epitopes are known to those of skill in the art to be recognized by T cells and not B cells and vice versa. Fourthly, epitopes can be selected on the basis of reactivity with immune serum or lymphocytes from individuals having an allergic or autoimmune response to an antigen. For example, an epitope known to be immunodominant or to stimulate a strong autoantibody response can be selected so that the portion of the antigen included in the fusion immunoglobulin includes that epitope. Fifthly, if there is little or no information known about epitopes on the antigen, it may be desireable to include the entire antigen in the fusion immunoglobulin.

The DNA sequence coding for an epitope can include an epitope of about 5–6 amino acids or an antigen having a molecular weight of up to about 100,000 daltons. The preferred size range is about 9 amino acids to about 50,000 daltons. For example, epitopes recognized by T cells have a consensus sequence including about 9 amino acids. It is believed that the minimal size of an epitope is about 5–6 amino acids. The maximum size of the antigen that can be presented in a fusion protein is the size that allows for the folding of both the antigen and the immunoglobulin carrier molecule. A preferred antigen is the A2 fragment of clotting factor VIII that has a molecular weight of about 40,000 daltons.

Once the epitope is selected and the DNA sequence encoding that epitope is obtained, the DNA sequence coding for the epitope is combined with the DNA sequence coding for the immunoglobulin to form a DNA sequence coding for a fusion immunoglobulin. The DNA sequence coding for the epitope is preferably combined with a DNA sequence for the immunoglobulin at the N-terminal variable region of the heavy chain in frame and in proper orientation. The location of the combination of the DNA sequence coding for the epitope can vary depending on the desired location of the epitope in the fusion immunoglobulin. If the epitope is the entire antigen or a large portion of the antigen (i.e., having a molecular weight of about 25,000 to about 100,000 daltons), the location of the epitope on the fusion immunoglobulin is such that it would allow folding of both the immunoglobulin carrier molecule as well as the antigen or the portion of the antigen. When the antigen and/or portion of the antigen is an epitope, it is preferably fused with the immunoglobulin at the amino terminus of the heavy chain at the amino acids at the N-terminus first framework region. Smaller epitopes (i.e., those containing about 5–50 amino acids) can be located at the first N-terminal framework region or within other regions on the variable portion of the immunoglobulin chain as long as the epitope remains exposed on the outer surface of the immunoglobulin molecule. Preferably, small epitopes can also be combined with the immunoglobulin at the amino acids of the first N-terminal framework region of the heavy chain.

Optionally, the DNA sequence coding for at least one heterologous tolerogenic epitope can include flanking DNA sequences on one or both ends of the DNA sequence. These flanking DNA sequences can include restriction endonuclease recognition sequences and/or can include a DNA sequence encoding a portion of the immunoglobulin sequence at the location where the two DNA sequences are to be combined. For example, a DNA sequence coding for an epitope that is combined at the first N-terminus framework region of a heavy chain of an immunoglobulin molecule can include a flanking DNA sequence encoding the first 5 amino acids of the first framework region on either or both ends of the DNA sequence coding for the epitope. The flanking DNA sequence can also include a recognition sequence for a restriction enzyme. The flanking DNA sequence is preferably about 3 to about 21 nucleotides long. When the flanking DNA sequence encodes a portion of the immunoglobulin amino acid sequence, that sequence is selected at the location of the point of combination of the epitopal DNA sequence with the immunoglobulin sequence. The flanking DNA sequence coding for a portion of the immunoglobulin amino acids can provide for amino acids in the fusion immunoglobulin that assist in the proper folding of both the epitope and/or antigen and the immunoglobulin at the point of fusion. The flanking DNA sequence can also insure that the DNA sequence coding for the epitope are combined with the DNA sequence coding for the immunoglobulin in frame and in proper orientation.

The DNA sequences coding for the immunoglobulin and the epitope are combined using standard subcloning methods. The combination of the two DNA sequences can be assisted by forming the DNA sequence encoding the epitope with flanking DNA sequences having certain restriction enzyme recognition sequences. These flanking sequences provide one of skill in the art with the ability to select the location at which the DNA sequence coding for the epitope will be combined with the DNA sequence coding for the fusion immunoglobulin and to insure the sequences are combined in frame and in proper orientation. When the DNA sequences coding for the immunoglobulin and the epitope are combined, they form a DNA sequence coding for a fusion immunoglobulin or a fusion heavy chain of an immunoglobulin molecule.

It should be understood that, due to the degeneracy of the genetic code, there are a number of DNA sequences that can code for an immunoglobulin and an epitope that have the same amino acid sequence. This set of sequences is a finite set and can be determined based on the amino acid sequence of the epitope and immunoglobulin. Alternative DNA sequences that code for an immunoglobulin molecule and an epitope with the same amino acid sequence are contemplated by and included within the scope of the invention.

The DNA sequence coding for a fusion immunoglobulin can then be combined with transcriptional and translational control regions functional in a hemopoietic or lymphoid cell. A control region that is important for expression of the DNA sequence coding for a fusion immunoglobulin includes a promoter. A suitable promoter is one that can function in a hemopoietic or lymphoid cell. The promoter preferably provides for constitutive expression of the DNA sequences coding for the fusion immunoglobulin. The promoter also preferably provides for an amount of the fusion immunoglobulin to induce and/or maintain tolerance. Suitable examples of promoters include the β-actin promoter, the SV40 promoter, and the LTR *Rous sarcoma* virus promoter.

Other transcriptional and translational control regions include enhancer sequences and transcription termination and polyadenylation sequences. Enhancer sequences can be combined with and are usually found within or adjacent to promoter sequences. Certain enhancer sequences, such as those from SV40, are active in many mammalian cells and provide for stimulation of transcription up to 1,000-fold from the homologous or heterologous promoters. Polyadenylation sequences are found downstream from the coding sequence and provide for proper formation of mRNA. Polyadenylation sequences can be obtained from SV40. Transcription termination sequences are found downstream from the polyadenylation sequences within a few hundred nucleotides.

These transcriptional and translational control regions are available in commercially available vectors. A DNA sequence encoding a fusion immunoglobulin or fusion heavy chain can be combined with transcriptional and translational control regions in frame and in proper orientation by subcloning into a vector having these control regions to form an expression cassette.

Vectors can be selected for the ability to provide for stable maintenance and/or gene expression in a hemopoietic or lymphoid cell. A vector is stably maintained in a cell if it can provide for expression of a fusion immunoglobulin over the lifetime of the cell. Stable maintenance can include maintenance and expression of a plasmid in a eukaryotic cell, preferably a cell such as a lymphoid cell. In that case, the plasmid including an expression cassette is not autonomously replicated or does not become integrated into the chromosome. The lifetime of a cell, such as a lymphoid cell, is about 14 to 60 days in the mouse or can be several years in humans. A plasmid vector containing an expression cassette can also be maintained in a lymphoid cell line such as the J558L cells without being replicated.

A vector can also be selected to provide for integration of the expression cassette into the chromosome of the host cell, such as a hemopoietic cell. In a hemopoietic cell from the bone marrow of an animal, the vector is introduced into a mixed population of cells, some of which are dividing cells and some of which have not yet begun dividing. The vector can integrate into the chromosome and then be replicated along with the chromosome and transferred to progeny cells. The vector is stably integrated if gene expression can be detected in the cell population at about 1 to 12 weeks after infected cells are introduced into an animal or cultured in vitro.

Suitable vectors include the plasmids such as pSNR1, pEMBL, pBR322, pRSA101, pUC118, pUC119, pBluescript, and pComb (Barbas et al., *PNAS*, 88:7978 (1991)). Suitable vectors also include viral vectors such as baculovirus and retroviral vectors such as the MBAE vector (Chambers et al., *PNAS*, 89:1026 (1992)). The preferred vector for hemopoietic cells is the MBAE vector.

A bacterial strain containing a plasmid vector having a DNA sequence that codes for fusion heavy chain has been designated *E. coli* DH5α (pQ3.EZ). The bacterial strain carries the plasmid pQ3.EZ which codes for fusion heavy chain that has a 12-26 amino acid epitope from λ-C1 repressor protein combined at the N-terminus first framework region of the heavy chain of an antibody specific for nitrophenyl. The bacterial strain has been deposited with the American Type Culture Collection at Rockville, MD on Feb. 7, 1994 and given Accession No. 69555.

In a preferred version, a DNA sequence coding for an epitope such as the 12-26 epitope from the λ-C1 repressor protein is combined with the DNA sequence coding for an immunoglobulin variable region at the first N-terminal framework region of the heavy chain to form a DNA sequence coding for a fusion heavy chain. The DNA sequence coding for a fusion heavy chain is combined with a β-actin promoter in an MBAE retroviral vector. The vector is preferably used to transform bone marrow cells or other B cell lineage cells that can produce light chains. The light chains combine with the fusion heavy chain to form a fusion immunoglobulin. Alternatively, a DNA sequence coding for a light chain could be included in the same vector as that coding for the fusion heavy chain to provide for expression of a fusion immunoglobulin.

B. Transformed Cells

Vectors containing expression cassettes coding for a fusion immunoglobulin are used to transform cells. The transformed cells are used in methods of identifying novel tolerogenic epitopes and to produce a fusion immunoglobulin. Transformed cells can also be introduced into animals for induction and maintenance of tolerance to the heterologous epitope expressed by the transformed cells or to an antigen containing the heterologous epitope.

Suitable cells for transformation include hemopoietic cells, lymphoid cells, and lymphoid cell lines. The cells include bone marrow cells, lymphoid cells, and the J558L lymphoid cells. Host cells are preferably those that are capable of forming and secreting immunoglobulin molecules. The cell population transformed preferably includes cells of B cell lineage and are those that synthesize light chains endogenously. Transformed cells that will be administered to animals are preferably syngeneic or share identical histocompatibility antigens to avoid rejection of the injected cells. For screening assays, bacterial host cells such as *E. coli* and the like can be suitable.

The vector can be introduced into cells using a variety of methods known to those of skill in the art such as calcium phosphate mediated transfection, polybrene mediated transfection, protoplast fusion, electroporation, and lipsomal mediated transfection.

Once the expression cassette is introduced into the cells, the transfected cells can be initially selected by detecting the presence of a selectable marker gene present on the vector. If the transfected cells are bone marrow cells or lymphoid cells, no selection may be employed. Transfected cells can then be screened for the presence and/or expression of the expression cassette coding for a fusion immunoglobulin. Transfected cells can be screened for the presence of an expression cassette using one or more techniques such as Southern blot, Northern blot, reverse transcriptase PCR, Western blot, ELISA, and immunofluorescence. Detectably labelled DNA probes can be used in Southern and/or Northern blots. The probes are sufficiently complementary to nucleotide sequences coding for the epitope or a portion of an antigen or an antigen so that the probe of about 50 to 100 nucleotides hybridizes under high stringency conditions. Primers for reverse transcriptase PCR can be designed as described previously to amplify cDNA sequences coding for the variable heavy and light chains of the immunoglobulin molecule.

Transfected cells in which the fusion immunoglobulin is being expressed can also be detected using a Western blot, ELISA or immunofluorescence. Amounts of fusion immunoglobulins being expressed can be detected using quantitative Western blot.

The amount of fusion immunoglobulin produced in a particular host cell type and with a particular promoter/enhancer sequence can be evaluated using a quantitative Western blot. The promoter/enhancer sequences providing for the most amount of constitutive expression of the fusion immunoglobulin can be determined by comparing the amount of fusion immunoglobulin produced in the same type of host cell over the same amount of time. A promoter/enhancer can be selected that would provide for a sufficient amount of fusion immunoglobulin to induce and/or maintain tolerance. The amount of a fusion immunoglobulin that will induce tolerance can vary in accordance with factors described herein and can be determined using standard methods.

C. Pharmaceutical Compositions

The invention also provides pharmaceutical compositions including a tolerogenic amount of a fusion immunoglobulin in a pharmaceutically acceptable excipient. The fusion immunoglobulin has at least one heterologous tolerogenic epitope on the N-terminal variable region of the immunoglobulin. Preferably, the heterologous tolerogenic epitope is combined with the immunoglobulin adjacent to the first N-terminal framework region of the heavy chain. The fusion immunoglobulin is combined with a pharmaceutically acceptable excipient in amounts effective to induce tolerance to the tolerogenic epitope or to an antigen containing the epitope in an animal. The pharmaceutical composition can be administered to an animal to induce and/or maintain tolerance to the tolerogenic epitope. Induction of tolerance to the epitope or epitopes can minimize animal allergic reactions or the symptoms of autoimmune disease.

Fusion immunoglobulins can be isolated from transformed cells using standard methods. Fusion immunoglobulins can be isolated from cell supernatants by passage through protein A or other affinity columns in accord with standard methods.

Suitable tolerogenic epitopes are those epitopes associated with allergic or autoimmune responses. A tolerogenic epitope is one that can be administered in such a way as to result in immunological unresponsiveness to the epitope and/or an antigen containing the epitope. If the epitope is one that stimulates an immunodominant response, tolerance to that epitope can also result in tolerance to an antigen containing the epitope. Specific examples include antigen E or antigen K of ragweed pollen, dust mite antigens, heterologous histocompatibility antigens, clotting factor VIII, acetylcholine receptors, myelin basic protein, and thyroglobulin. The fusion immunoglobulin can contain a single tolerogenic epitope or a multiple tolerogenic epitopes. Preferably, the tolerogenic epitope is an epitope that is immunodominant in the allergic or autoimmune response.

The amount of the fusion immunoglobulin effective to induce tolerance in an animal depends on a factors but can be readily determined by one of skill in the art using standard dose response methods. The factors include the size of the animal to be treated, the number and type of epitopes, the type of tolerance, the age of the animal, the route and number of times of administration, and the duration of the tolerance desired.

The age of the animal can be an important factor in determining the effective tolerogenic amount of an epitope. A neonatal or infant animal may require about 100 to 1000-fold less of a single dose of a fusion immunoglobulin administered intravenously than that required by an adult of the fusion immunoglobulin in order to induce tolerance to the epitope.

A tolerogenic amount of a fusion immunoglobulin also depends on the size of the animal and is typically about 10 to 100-fold higher (for B-cell tolerance) than the amount of the antigen and/or epitope given to the animal to elicit a protective immune response, except in the case of low dose tolerance. A tolerogenic amount of an antigen per unit of mass is typically about 1 to 40 mg/kg of body weight to induce high dose tolerance for an epitope or antigen administered as a single dose intravenously to an animal. Low dose tolerance is also observed in some cases and can be obtained after multiple (>4) doses of submicrogram quantities in saline at weekly intervals intraperitoneally or intravenously.

Another factor that can vary the tolerogenic amount of a fusion immunoglobulin is whether the fusion immunoglobulin includes more than one epitope and whether those epitopes are immunodominant. If the fusion immunoglobulin has multiple epitopes, some of which are immunodominant, about a 10-fold lower dose of fusion immunoglobulin can induce tolerance when administered as a single dose to an animal intravenously.

The tolerogenic amount of a fusion immunoglobulin can also vary depending on whether a T cell or B cell tolerance is desired. Typically, T cell tolerance requires a dose of antigen or epitope about 10 to 100-fold less than for B cell tolerance to that same epitope or antigen.

Another factor is the persistence of the fusion immunoglobulin in the animal's circulation. A more slowly metabolized antigen provides for maintenance of tolerance for longer periods of time, typically about 2 to 10-fold greater time of maintenance of tolerance. The catabolic rate of epitopes or antigens depends on the half-life of isologous or the heterologous carrier immunoglobulin as well as the nature of the epitope or epitopes. The half-life rate of isologous or heterologous immunoglobulin is about 7 to 21 days (mouse). Epitopes having modified or unusual amino acids, such as D amino acids as well as complex antigens or epitopes, may not be degraded as rapidly as other types of epitopes.

Mode of administration can also influence the tolerogenic amount of the fusion immunoglobulin necessary. In the usual case, intravenous administration is the preferred route for inducing tolerance. The number of times the antigen is administered can also influence the amount of fusion immunoglobulin required per administration.

An effective tolerogenic amount for a particular heterologous tolerogenic epitope on a fusion immunoglobulin can be determined by conducting in vivo or in vitro dose response assays. The in vitro dose response assays can be conducted, for example, by using standard lymphocyte proliferation assays. For example, lymphocytes from an allergic or autoimmune animal can be combined with different doses of the fusion immunoglobulin and proliferation measured.

In vivo dose response can be determined by administering different doses of the fusion immunoglobulin in an excipient to an animal. The lack of immune responsiveness to the heterologous tolerogenic epitope can be determined by measuring the specific antibody response to the heterologous tolerogenic epitope or lymphocyte proliferation to a challenge dose of the fusion immunoglobulin.

Induction of tolerance is evaluated by measuring a decrease in immunological unresponsiveness. Methods of measuring immunological responsiveness can be conducted with in vivo or in vitro antigen presentation and challenge and are known to those of skill in the art. For example, the amount of antibody specific to the epitope and/or antigen can be measured as well as lymphocyte proliferation in response to a challenge with the epitope or fusion immunoglobulin. The decrease in immunological responsiveness that indicates tolerance has been induced can be about 2-fold to 100-fold, preferably about 20-fold to 100-fold reduction in antibody or lymphocyte responsiveness. The range of the decrease can vary depending on the sensitivity of the assay used to measure immunological responsiveness. For example, it is known that a decrease in the number of antibody-producing cells is more sensitive than a decrease in the amount of antibody. The range of the decrease can also vary if the epitope is an immunodominant epitope. A 2-fold change in responsiveness to an immunodominant epitope can result in significant levels of tolerance to the epitope and/or an antigen containing the epitope.

A single dose of a fusion immunoglobulin can induce tolerance. In some cases, the tolerance induced by a single dose in the mouse can last from about 2 months to about 6 months. However, for tolerance to be maintained in an animal, multiple doses are typically required. Maintenance of tolerance can be desired for at least that amount of time induced by a single dose of the fusion immunoglobulin to throughout the lifetime of the animal.

A tolerogenic amount of the fusion immunoglobulin is combined with a physiological excipient such as saline, buffered saline and incomplete Freuds adjuvant. The fusion immunoglobulin can be administered by a variety of routes such as intraperitoneally, orally, and intravenously but is preferably administered by the intravenous route. The animals that can be treated to induce tolerance to allergens or auto-antigens include mice, humans, rats, rabbits and guinea pigs.

D. Methods of Identifying Epitopes That Can Serve as Tolerogens

The invention also provides methods of identifying epitopes that can serve as tolerizing epitopes. Identification of novel tolerogenic epitopes could be useful in diagnosis and treatment of autoimmune and allergic immune responses. One method includes the steps of providing a vector including a DNA sequence coding for a fusion immunoglobulin operably linked to transcriptional and translational control regions functional in a host cell. The fusion immunoglobulin has at least one heterologous epitope at the N-terminus variable region. The epitope can be one that is suspected of being able to induce tolerance. Cells are stably transformed with the vector as described previously. Transformed cells expressing the fusion immunoglobulin or the isolated fusion immunoglobulin are analyzed for the ability to immunoreact with immune serum or lymphocytes from allergic or autoimmune animals. Tolerance induction to a fusion immunoglobulin identified by reactivity with immune serum or lymphocytes for autoimmune or allergic animals can be evaluated by in vitro or in vivo methods known to those of skill in the art. For example, fusion immunoglobulins that react with immune serum and/or stimulate lymphocyte proliferation can be administered to an animal and induction and maintenance of tolerance can be assessed as described herein.

In another method, the transformed hemopoietic or lymphoid cells can be introduced into an animal and induction and maintenance of tolerance to the heterologous epitope can be determined using assays for evaluating specific immunological responsiveness to the epitope as described previously.

Some epitopes and antigens are known to elicit immune responses. Some epitopes and antigens are known to elicit immunodominant immune responses associated with allergic or autoimmune immune responses. Those epitopes that elicit immune responses may or may not induce tolerance when presented in a fusion immunoglobulin. Epitopes of some antigens known to be associated with allergic or autoimmune immune responses have not been identified. The methods of the invention can be utilized to determine whether an epitope known to elicit an immune response can induce tolerance when presented in a fusion immunoglobulin or to identify novel tolerogenic epitopes of antigens.

In one method, a vector comprising a DNA sequence coding for a fusion immunoglobulin operably linked to transcriptional and translational control regions functional in the hemopoietic or lymphoid cell is transformed into a hemopoietic or lymphoid cell. The fusion immunoglobulin can include an epitope known to elicit an immune response or a novel tolerogenic epitope. The promoter/enhancer sequences preferably provide for expression of the fusion immunoglobulin in a hemopoietic or lymphoid cell at a level sufficient to induce tolerance to the epitope in vivo or in vitro. Such a promoter can be identified and screened for in an in vitro assay as described herein. The amount of fusion immunoglobulin that can induce tolerance in animals can be determined using standard dose response methodology.

The transformed cells are introduced into an animal. When transformed hemopoietic cells are introduced into an animal, preferably the animal has been irradiated before introduction of the transformed cells to destroy endogenous hemopoietic cells. The transformed cells are administered to an animal by intraperitoneal or intravenous injection. The animals are then analyzed for induction of tolerance to the epitope after about 2 to 20 days. Tolerance can be detected by measuring the specific antibody response or lymphocyte proliferation response to the heterologous tolerogenic epitope. A decrease in the specific antibody or lymphocyte proliferative response to the epitope of about 2 to 100-fold, preferably 10- to 100-fold, indicates tolerance to the epitope.

Preferably, the screening assays for identifying tolerogenic epitopes are conducted in mice. The transformed cells can be syngeneic mouse cells derived from another genetically identical mouse, or can be human hemopoietic or lymphoid cells. For example, screening assays can be done using human bone marrow tissue transformed with a vector. The human bone marrow tissue is then administered to immunodeficient mice such as the SCID—SCID mice according to the method described by Chambers et al., cited supra. Tolerance can be evaluated in the SCID—SCID mice by examining either the specific antibody response to the epitope or the lymphocyte proliferation response.

Another method of the invention provides for screening for novel tolerogens, preferably those associated with autoimmune or allergic immune responses. In this method, epitopes of antigens associated with allergic or autoimmune responses are screened for the ability to immunoreact with immune serum or to stimulate lymphocyte proliferation from animals having an allergic or autoimmune response. For example, different cDNA sequences coding for portions of a complex antigen such as clotting factor VIII can be combined with a DNA sequence coding for N-terminus variable region of an antibody to form a library of cDNA sequences coding for fusion immunoglobulins with different epitopes derived from clotting factor VIII. The DNA sequences coding for epitopes can be generated randomly, or can be selected to encode overlapping linear amino acid sequence, or can be selected based upon the likelihood that the amino acids encoded by the DNA sequence are exposed (based on tertiary structure) on the surface of the clotting factor VIII molecule. The cDNA sequences coding for different portions of the antigen can be combined with cDNA sequences for the N-terminus variable region of an immunoglobulin, preferably at the first N-terminus framework region of the heavy chain as described previously.

A phagemid vector system such as pComb can be used to generate a cDNA library of heavy and light chains of antibodies having cDNA sequences coding for different portions of an antigen combined as described above. The phagemid vector can be constructed to carry these cDNA sequences using standard restriction enzyme digestion and ligation methods as described in Barbas et al., *PNAS*, 88:7978 (1991). The phagemid library can be screened for immunoreactivity with immune serum from allergic or autoimmune animals in a panning and/or filter Western blot assay similar to those described by Barbas et al., cited supra.

Briefly, the phagemid vectors carrying the Fab fragments with at least one heterologous epitope derived from an antigen are transformed into a *E. coli* strain. The *E. coli* strain is grown in the presence of antibiotics to select for those strains carrying the phagemid vector. Phage can be isolated and then screened for binding to wells coated with immune serum from an allergic or autoimmune animal as described by Barbas et al., cited supra. Adherent phage are eluted using elution buffer. Eluted phage can be transferred into *E. coli* cells and colonies can be examined for the presence of a phagemid carrying a Fab fragment with a heterologous epitope using a filter Western blot type assay with immune serum from an allergic or autoimmune animal.

Phagemid DNA from positive clones can be isolated and the DNA sequence coding for the fusion Fab can be subcloned into a vector that can be used to transform hemopoietic or lymphoid cells. The vector can contain additional DNA sequences so that a fusion immunoglobulin rather than Fab fragment is produced by the transformed cells. The fusion immunoglobulin having a heterologous epitope that reacts with immune serum from allergic or autoimmune animals from a positive clone identified as described can be isolated and tested for the ability to induce tolerance in vitro or in vivo. Alternatively, transformed cells carrying such a vector can be introduced into an animal and induction of tolerance in vivo can be determined as described herein.

Once novel epitopes and/or fusion immunoglobulins that can induce tolerance are identified, they can be used in pharmaceutical compositions and methods for tolerizing animals to the epitopes. Alternatively, the identification of novel tolerogenic epitopes associated with autoimmune or allergic immune responses could be used in standard diagnostic assays to assess the presence of autoimmune or allergic immune responses or to monitor the effectiveness of treatment.

E. Methods of Tolerizing an Animal to an Epitope

The invention also provides methods for inducing and maintaining tolerance to an epitope in an animal. In one method, a pharmaceutical composition including a fusion immunoglobulin is administered to an animal as described previously. In another method, tolerance can be induced and maintained in an animal by introducing transformed hemopoietic or lymphoid cells producing the fusion immunoglobulin into the animal. Without limiting the invention in any way, it is believed that the persistent production of fusion immunoglobulin carrying the heterologous epitope by the transformed cells in vivo can allow for maintenance of tolerance as well or better than using a pharmaceutical composition of the fusion immunoglobulin.

In one method, a vector coding for a fusion immunoglobulin that can be stably maintained in a hemopoietic or lymphoid cell is provided. The fusion immunoglobulin has at least one heterologous tolerogenic epitope. Hemopoietic or lymphoid cells, such as peripheral blood cells, are transformed with a vector such as MBAE using polybrene. Transformed cells are not typically selected and the entire population of hemopoietic or lymphoid cells are administered to the animal. Transformed cells can be evaluated for production of a fusion immunoglobulin in vivo or in vitro by detecting the presence of fusion immunoglobulin using antibodies or by detecting expression of fusion immunoglobulin mRNA using RT-PCR or Northern blots. Preferably, the transformed cell population is analyzed in vitro for production of fusion immunoglobulin at a level sufficient to induce and maintain tolerance to the heterologous epitope in an animal.

Transformed cell population prepared so that the fusion immunoglobulin is produced at a level sufficient to induce and/or maintain tolerance are introduced into an animal. The amount of cells introduced into the animal is that amount that provides for production of a fusion immunoglobulin at a level sufficient to induce tolerance, and preferably to maintain tolerance. The animal is monitored for induction and persistence of tolerance to the heterologous epitope using assays as described previously. In some cases, the animals are irradiated sufficiently to destroy endogenous hemopoietic or lymphoid cells before introduction of the transformed cell populations. An animal is considered tolerant to the epitope if about a 2-to 100-fold decrease in immunological responsiveness, such as lymphocyte proliferation or antibody response, is seen. Tolerance is considered to be maintained if the tolerant state is maintained at least as long as the tolerant state induced with a single intravenous injection of a tolerogenic pharmaceutical composition. In mice, a single injection of a tolerogenic amount of a fusion immunoglobulin can result in tolerance of about 2 to 20 days and as long as about 2 months to 6 months. Tolerance could be maintained throughout the lifetime of the animal.

Suitable transformed cells include bone marrow cells and lymphoid cells from mice or humans. Suitable animals include inbred strains of mice including immunodeficient mice such as the SCID—SCID mice. Induction and maintenance of tolerance to epitopes using human transformed cells can be evaluated by the development of tolerance to epitopes in human transformed cell populations administered to SCID—SCID mice. Other transformed animal cells, such as bovine transformed cells, can also be evaluated for the induction of tolerance in SCID—SCID mice.

In another method, a tolerogenic amount of a fusion immunoglobulin can be used to induce tolerance and tolerance can be maintained by administration of transformed hemopoietic or lymphoid cells expressing the same fusion immunoglobulin. In the method, a tolerogenic amount of a fusion immunoglobulin can be administered as a single dose as described herein. After a state of immunological unresponsiveness is obtained, transformed hemopoietic or lymphoid cells expressing the fusion immunoglobulin can be administered to the animal. While not meant to limit the invention, it is believed that the transformed hemopoietic or lymphoid cells will result in the maintenance of tolerance to the epitope. The amount of fusion immunoglobulin that needs to be expressed when transformed cells are used to maintain rather than induce tolerance can be less than that required of cells that both induce and maintain tolerance. Typically, administration of about 10 to 100-fold less of the fusion immunoglobulin or antigen is required to maintain rather than induce tolerance.

EXAMPLE I

Preparation of Fusion Immunoglobulin p12-26 Recombinant Constructs

Figure 1B:
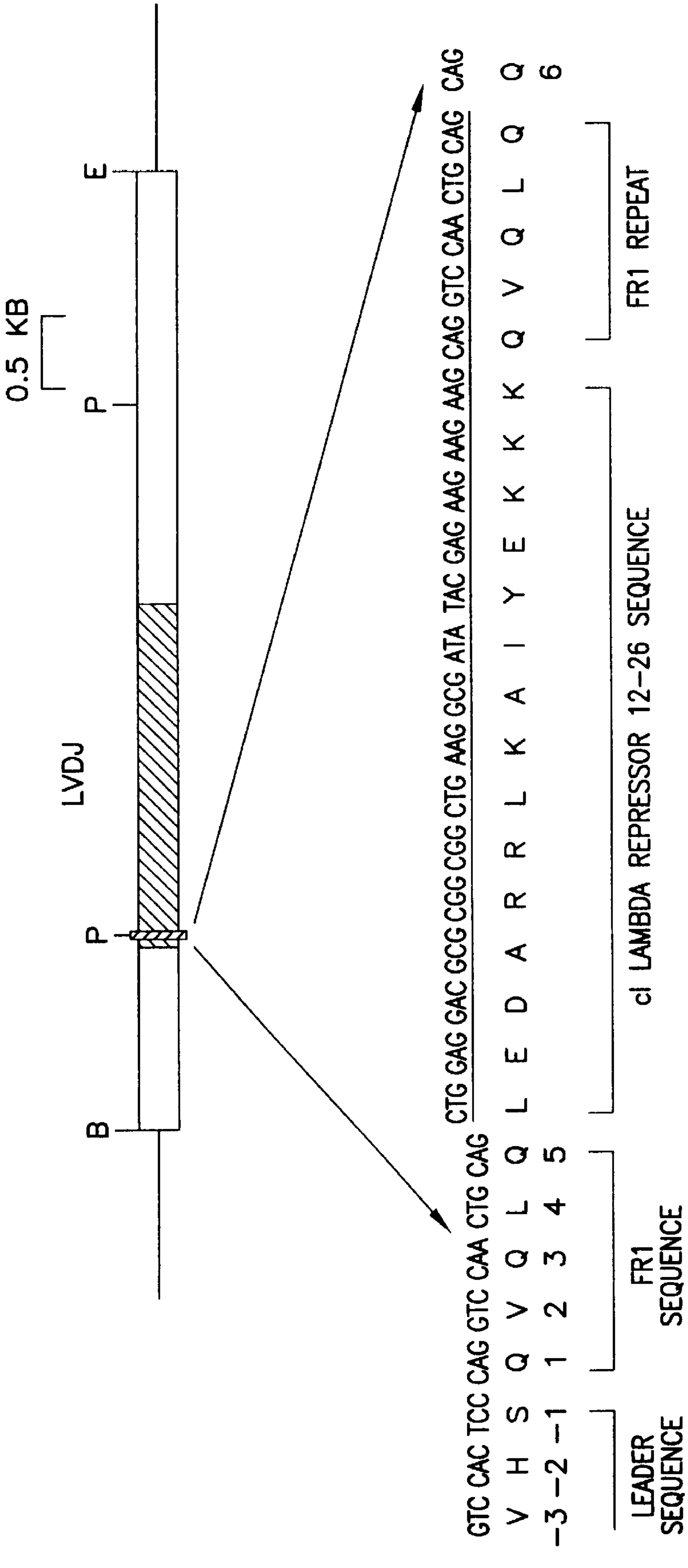

Tolerance to the epitope comprising residues 12-26 of the bacteriophage λ cI protein was studied because this epitope can be recognized by both T and B cells, and it is the major immunodominant epitope of this protein in H-$2^d$ mice. This epitope was expressed in a fusion protein of mouse IgG having the epitope at the N-terminus. Isologous IgG1 was chosen for the fusion protein because it is known to be a tolerogenic carrier. Isologous immunoglobulins (especially IgG's) are likely to make efficient tolerogenic carriers because of their ability to crosslink B-cell Fc receptors and to persist in the circulation, as well as their lack of "intrinsic immunogenicity", that is, the lack of the potential to elicit an immune response in a soluble form. DNA constructs coding for a fusion polypeptide of immunoglobulin IgG containing the 12-26 epitope of λ cI repressor protein were obtained by modifying plasmid pSNR-1. (See FIG. 1.)

The major immunodominant peptide of the λ cI repressor protein (residues 1-102) is found at residues 12-26, as described in *Nature*, 343:381 (1990). The DNA sequence coding for this peptide fragment was synthesized by standard automated methods. The synthetic oligonucleotide fragment coding for the 12-26 epitope has the following sequence (SEQ ID NO:1):

5' CTG GAG GAC GCG CGG CGG CTG AAG GCG ATA TAC GAG AAG AAG AAG 3'

3' GAC CTC CTG CGC GCC GCC GAC TTC CGC TAT ATG CTC TTC TTC CCT 5'

The corresponding amino acid sequence encoded by this fragment is:

Leu-Glu-Asp-Ala-Arg-Arg-Leu-Lys-Ala-Ile-Tyr-Glu-Lys-Lys-Lys (SEQ ID NO:2)

Plasmid pSNR-1 is a plasmid that includes a DNA sequence coding for the variable heavy chain domain (VH) and heavy chain constant regions 1–3 (CH1–3) from a murine immunoglobulin specific for 4-hydroxy-3-nitrophenyl. Plasmid pSNR-1 was constructed as described by Ballard et al., *PNAS*, 83:9626 (1986). The pSNR-1 plasmid was obtained from Douglas Fearon (Johns Hopkins, Baltimore, Md.). To introduce the DNA sequence coding for the 12-26 epitope into the N-terminus of the variable heavy chain, the plasmid PSNR was manipulated as described below. A 1.3 kbp region of the pSNR-1 plasmid including the coding sequence for VH, 118 bp of DNA sequence 5' upstream promoter element to the VH coding sequence coding for a promoter element, and 3' downstream intron and IgH enhancer sequences was subcloned using standard methods. This sequence is defined between restriction enzyme sites BamHI and EcoRI, and was subcloned into the plasmid pBS (Stratagene) using BamHI and EcoRI restriction endonucleases. The pBS/VH was digested with PstI under conditions to isolate a single cut PstI partial digest fragment, as described in *Current Protocols in Molecular Biology*, cited supra.

The 12-26 epitope was modified and then inserted into the VH region of the immunoglobulin at a location that provided for proper folding of that region. The DNA sequence coding for the 12-26 epitope was modified by adding the coding sequence for the first 5 amino acids of the framework region (FRI) of the VH coding sequence at the 3' end of the synthetic DNA sequence coding for the 12-26 epitope. This modification allowed for proper folding and was selected to result in minimal disruption in the tertiary structure of the immunoglobulin molecule. Regions of the Ig molecule that are likely to be sites where insertion of an epitope are not likely to disrupt the molecule can be determined by analyzing the amino acid sequence of the Ig molecule as well as the tertiary structure. The N-terminal and CDR regions on the Ig chain are preferable regions into which the epitopes can be inserted to result in minimal disruption of the tertiary structure. Insertion at the N-terminal region allows for insertion of larger polypeptide ≧ 10 kDa.

The modified 12-26 sequence including the sequence for the first five amino acids of the first framework region of the VH was obtained via polymerase chain reaction. A plasmid containing the 45 base pair nucleotide sequence coding for the 12-26 epitope was constructed by cloning the synthetic 45 base pair DNA sequence into the BamHI/ClaI site of a plasmid pPX1647 containing the H-ld flagellin gene (provided by Dr. P. Brey, Praxis-Lederle Corp.), a derivative plasmid of pUC119. The modified 12-26 sequence was amplified using PCR techniques and two primers.

The primers were designated OS-1 and OS-2. The primer OS-1 contains the coding sequence for the PstI site and the coding sequence for the first 5 amino acids of the 12-26 sequence. The sequence for OS-1 (SEQ ID NO:3) is:

5' TGATCTACTG CAGCTGGAGG ACGCGCGGCG G 3'.

The primer OS-2 was complementary to the coding sequence for the PstI site and to the coding sequence for the first 5 amino acids of the first framework region of VH and the last 6 amino acids of the 12-26 sequence. The sequence for OS-2 (SEQ ID NO:4) is:

5' CGACCTCCTG CAGTTGGACC TGCTTCTTCT TCTCGTATAT 3'.

The 82 bp product of the PCR method, i.e., the modified 12-26 sequence, was isolated by high sieve agarose using standard methods.

The 82 base pair PCR fragment was digested with PstI to produce a 65 bp fragment coding for the modified 12-26 epitope including the first 5 amino acids of FR1. The 65 bp fragment was subcloned into the plasmid pBS at a pST1 site. The subcloning was done by digesting the modified 12-26 sequence with PstI. The selected plasmids containing the PstI fragment of modified 12-26 were sequenced to confirm the presence of that fragment in proper orientation. Plasmids containing the modified 12-26 sequence are referred to as pBS/12-26 and were sequenced to confirm structure.

The modified 12-26 fragment from pBS/12-26 was subcloned into pBS/VH. The subcloning was performed by initially doing a partial PstI digest of the pBS/VH to cut the VH region at a PstI site, which is located at the coding sequence for the first framework amino acids 4 and 5 of VH. The pBS/12-26 was fully digested with PstI. After ligation, plasmids containing the modified 12-26 sequence inserted after the coding sequence for the first 5 amino acids of the first framework region of the VH were selected by filter hybridization of bacterial colonies using a $p^{32}$ labeled 12-26 oligonucleotide as probe. The resulting VH fusion sequence is as follows: L-FRI-12-26-FRI (L=leader sequence; FRI= the first 5 amino acids of the first framework region of VH). Double stranded sequencing was done to confirm proper site insertion as well as orientation. These plasmids are designated pBS/VH/12-26.

The presence of the VH/12-26 recombinant sequence in the plasmid was verified by DNA sequencing methodologies. The VH DNA sequence surrounding and including the modified 12-26 insert (SEQ ID NO:5) is as follows:

```
CAG GTC CAA CTG CAG CTG GAG GAC GCG CGG CGG CTG AAG GCG
                     L   E   D   A   R   R   L   K   A

ATA TAC GAG AAG AAG AAG CAG GTC CAA CTG CAG
I   Y   E   K   K   K
```

The modified 12-26/VH recombinant from pBS/VH/12-26 was subcloned into a plasmid pSV2-neo at the BamH1/ECORI sites. The pSV2-neo plasmid is derived from pSNR (Dr. Al Bothwell, Yale University New Haven, CT) and contains the $V_H$ (NP-binding) inserted in an $IgG_1$, heavy chain. The 8.5 kbp EcoRI fragment from pSNR-1 and which contains the constant regions 1–3 (CH 1–3) of $\alpha_1$ chain was also subcloned into the pSV2-neo. Deletion of a 8.5 kbp region between the EcoRI sites of plasmid pSNR-1, which includes the CH1–3 coding sequence, was carried out using standard techniques as disclosed in *Current Protocols in Molecular Biology*, Vol. 1: Supplement 3.1.3, John Wiley & Sons (1989). The complete plasmid contains the sequence coding for the variable heavy chain with the 65 base pair sequence coding for the 12-26 epitope inserted at the N-terminus first framework region of the variable heavy chain and the sequence coding for the (CH1–3) constant regions 1–3. The orientation of the modified variable region sequence and the constant regions were verified by Southern restriction analysis, as described in *Current Protocols in Molecular Biology*, cited supra. Successful recombinants were selected by ampicillin and a large scale plasmid preparation was grown using standard methods.

EXAMPLE II

Expression of Fusion Immunoglobulin p12-26 Recombinant Constructs

The recombinant plasmids containing the coding sequence for both the VH/12-26 fusion and the CH1–3 of IgG1were introduced into host cells and expression of the fusion protein was detected. Transformation and detection of expression was carried out using standard methods as described in *Current Protocols in Molecular Biology*, cited supra.

The 12-26 IgG1DNA construct (Q3) as well as the control pSNR construct (P6) were electroporated into J558L myeloma cells which synthesize only λ light chains. Stable integrants were selected for growth in the presence of the antibiotic G418. Transfectomas expressing the 12-26 IgG1fusion protein were identified by analyzing cell culture supernatants by Western blot and ELISA.

Transfectomas were grown to high density in serum-free media (RPMI-1640 with 5% FCS) in roller bottles and in bulk culture. Purification from serum-free transfectoma supernatants was accomplished successfully via binding with protein-A sepharose at pH 8, with elution at pH 4, as well as with anti-mouse IgG affinity columns.

Figure 2:
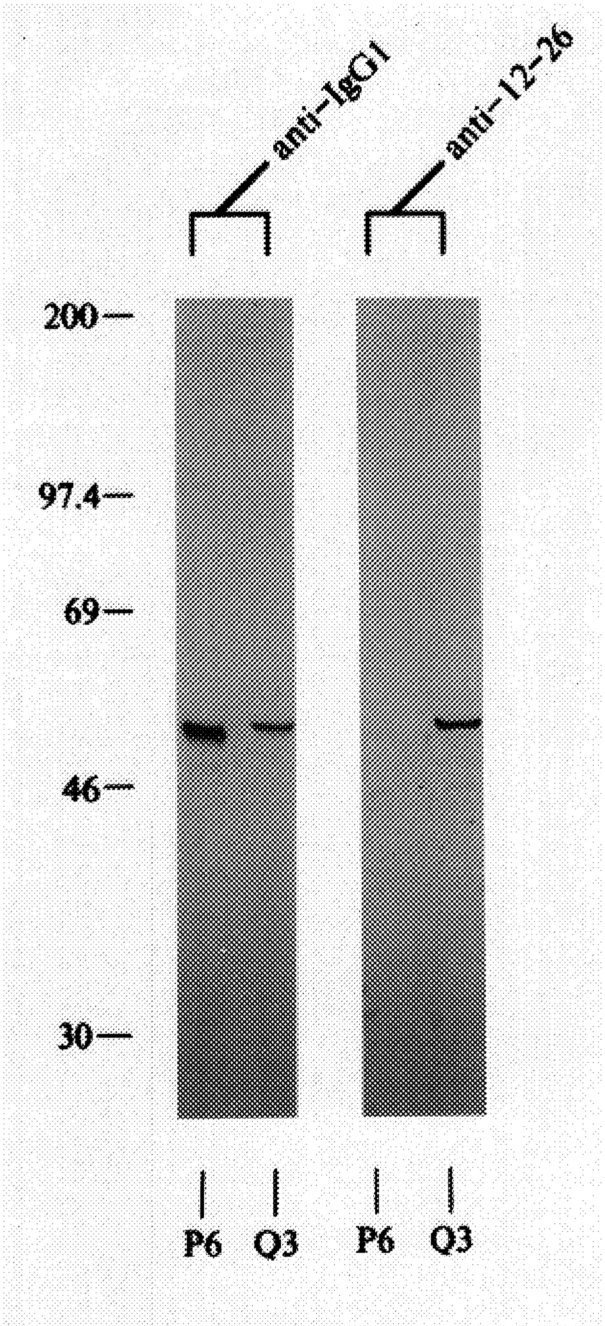
FIG. 2: Detection of a heterologous epitope on the 12-26-IgG fusion protein. The 12-26-IgG1 construct (Q3), as well as the control pSNR construct (P6) were electroporated into J558L myeloma cells, which synthesize only λ light chains. Recombinant IgG's were purified from bulk supernatants of transformed cells with anti-mouse IgG-sepharose or protein-A-sepharose columns. Western blotting: samples were electrophoresed on 10% SDS-PAGE. Gels were transferred to nitrocellulose and probed with anti-mouse IgG (left lanes) or with anti-12-26 monoclonal antibody B3.11 (right lanes) plus alkaline phosphatase-conjugated antibodies as secondary reagents.
Figure 3:
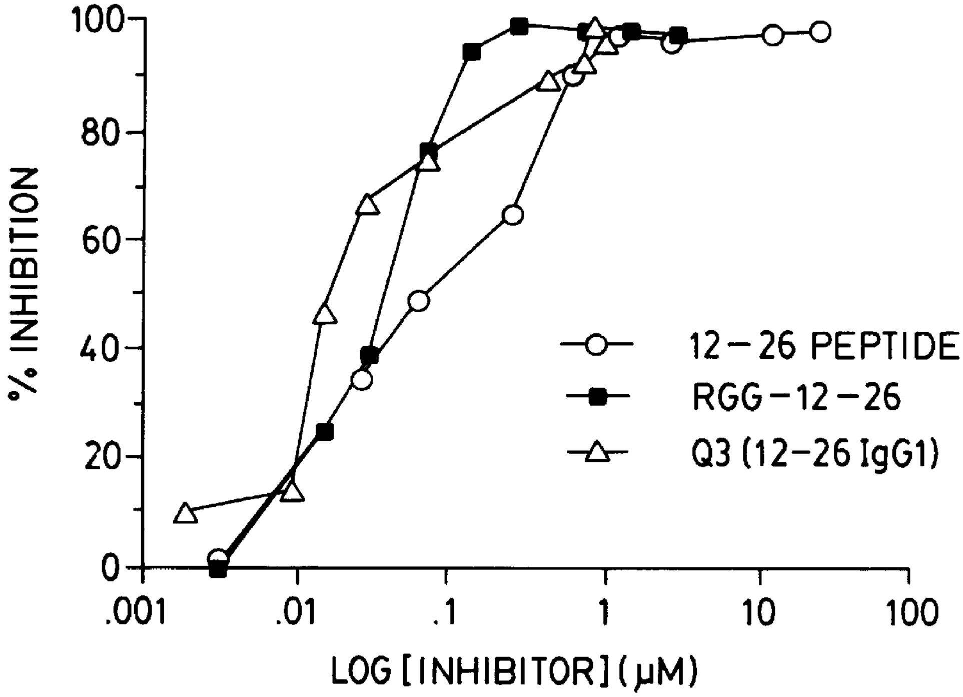
FIG. 3: ELISA inhibition curves. Pre-titrated monoclonal antibody B3.11 was mixed with increasing amounts of 12-26 peptide, 12-26 peptide chemically coupled to rabbit gamma globulin (RGG/12-26), or Q3 (recombinant fusion protein 12-26 IgG1).

Purified supernatants from selected clones have been analyzed for expression of 12-26 epitopes by Western blotting and ELISA by standard methods. (See FIGS. 2 and 3.) For Western blotting, samples were electrophoresed on 10% SDS-PAGE. Gels were transferred to nitrocellulose and probed with anti-mouse IgG (left lanes) or anti-12-26 monoclonal antibody B3.11 (right lanes) plus alkaline phosphatase-conjugated antibodies as secondary reagents. The results are shown in FIG. 2. Only those cell culture supernatants from transfectomas containing the 12-26 IgG1construct (Q3) reacted with antibodies specific for mouse IgG (left lanes) and antibodies specific for the 12-26 epitope the 12-26 epitope (right lanes).

For ELISA competitive inhibition assays, pre-titrated monoclonal antibody B3.11 was mixed with increasing amounts of 12-26 peptide, or the 12-26 peptide chemically coupled to rabbit gamma globulin (RGG/12-26), or 12-26 IgG1(Q3). The ability of the mixtures to bind to immobilized 12-26 peptide was determined by standard methods. The results, shown in FIG. 3, indicate that the 12-26 IgG fusion protein was able to effectively inhibit the binding of the monoclonal antibody to the 12-26 epitope compared with the 12-26 peptide in solution.

The competitive inhibition ELISA studies show that these fusion immunoglobulins can effectively compete with free synthetic peptide or 12-26 chemically-conjugated to rabbit IgG for binding to monoclonal antibody anti-12-26 B3.11. In addition, the 12-26-IgG is immunogenic for the 12-26 epitope when emulsified in CFA (data not shown). This suggests that the inserted peptide can be processed and presented in a physiologically relevant manner even in the context of a self-IgG molecule. Experiments also indicate that the 12-26 fusion immunoglobulins can stimulate IL-2 production (measured by CTLL assay) in an H-$2^d$ restricted 12-26 specific T-cell hybridoma (9C127) (data not shown).

EXAMPLE III

Tolerance Induction in Mice with the 12-26 IgG1 Fusion Protein

A high dose pretreatment of animals with the 12-26 peptide injected intravenously or intraperitoneally in saline or emulsified in incomplete Freund's adjuvant (IFA) can induce T-helper cell tolerance upon subsequent immunization with peptide in complete Freund's adjuvant (CFA). Scherer et al., *Symp. on Quant. Biol.*, Cold Spring Harbor, N.Y., 54:497 (1989) Tolerance induction to the 12-26 epitope has been confirmed in T-cell proliferation assays. However, animals treated with peptide are not tolerant at the B-cell level. That is, when challenged with 12-26-flagellin (providing "carrier epitopes"), the response was not diminished (see below). This indicates the reductions with peptide challenge were due to T- but not B-cell tolerance.

Figure 4:
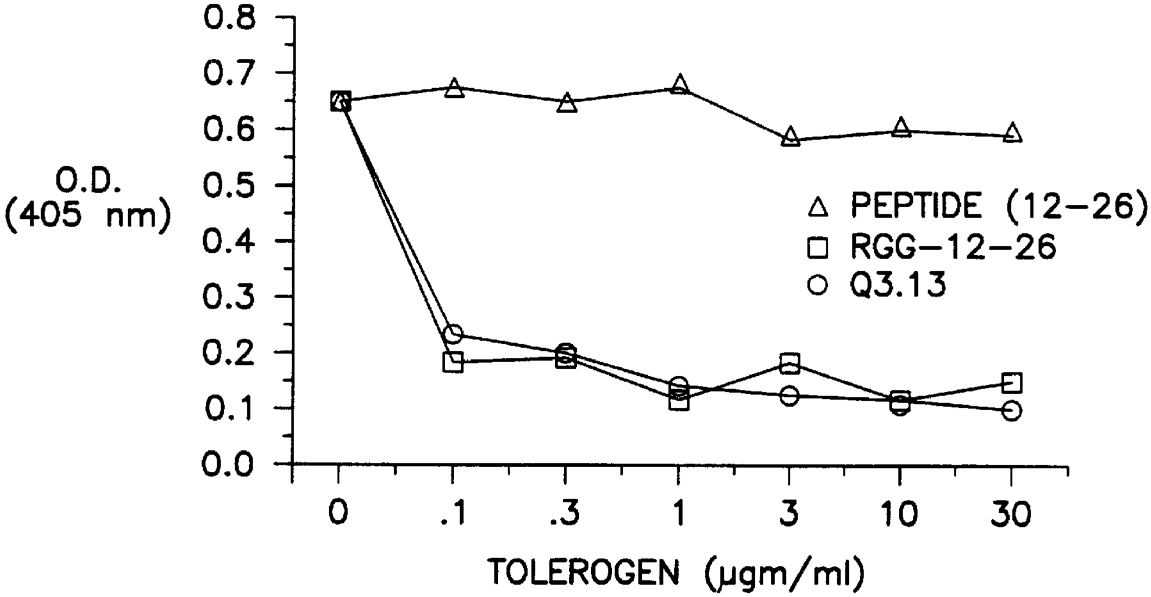
FIG. 4: Tolerance induction by 12-26-IgG fusion protein as determined in vitro. Spleen cells were cultured for 18 hours with increasing amounts of 12-26 peptide or 12-26-IgG fusion protein (Q3.13) or a 12-26-rabbit gamma globulin (RGG) conjugate. Cells were then washed and challenged with an antigen containing the 12-26 epitope (12-26-fagellin) and ELISA assays were done on day 4 supernatants.

To determine whether the 12-26 IgG1fusion protein can induce B-cell tolerance, the following experiment was conducted. Mouse spleen cells were cultured in vitro in RPMI-1640+5% FCS for 18 hours. The mouse spleen cells were then incubated with increasing concentrations of either free 12-26 peptide, a chemical conjugate of rabbit gamma globulin with 12-26 (RGG-122-26) or with 12-26-IgG1(Q3). At 18 hours, these spleen cells were washed and then challenged with either lipopolysaccharide (a mitogenic stimulus, not shown) or the A29 fusion protein of *Salmonella flagellin* that contains the 12-26 peptide. The *Salmonella flagellin* fusion protein containing the 12-26 epitope has been shown previously to be immunogenic both in vivo and in vitro (data not shown). As a control for induction of tolerance, spleen cells were treated with a rabbit anti-immunoglobulin previously shown to induce unresponsiveness in vitro. G. Warner et al., *J. Immunol.*, 146:2185 (1991). The effect of anti-Ig is shown as an open circle on the right end of each graph. The responsiveness of the cells was measured by ELISA. The results are shown as FIG. 4 (A29 fusion protein with 12-26 peptide challenge).

The results indicate that when spleen cells are challenged with the A29 fusion protein, the 12-26 IgG1 fusion protein (Q3.13), or the chemical conjugate (RGG-12-26) were both tolerogenic at microgram levels. In contrast, the free peptide does not inhibit B-cell responsiveness at any dose. Thus, these results indicate that the 12-26 IgG fusion proteins can induce tolerance in B-cells in vitro. Similar results were obtained in vivo as follows.

Figure 5:
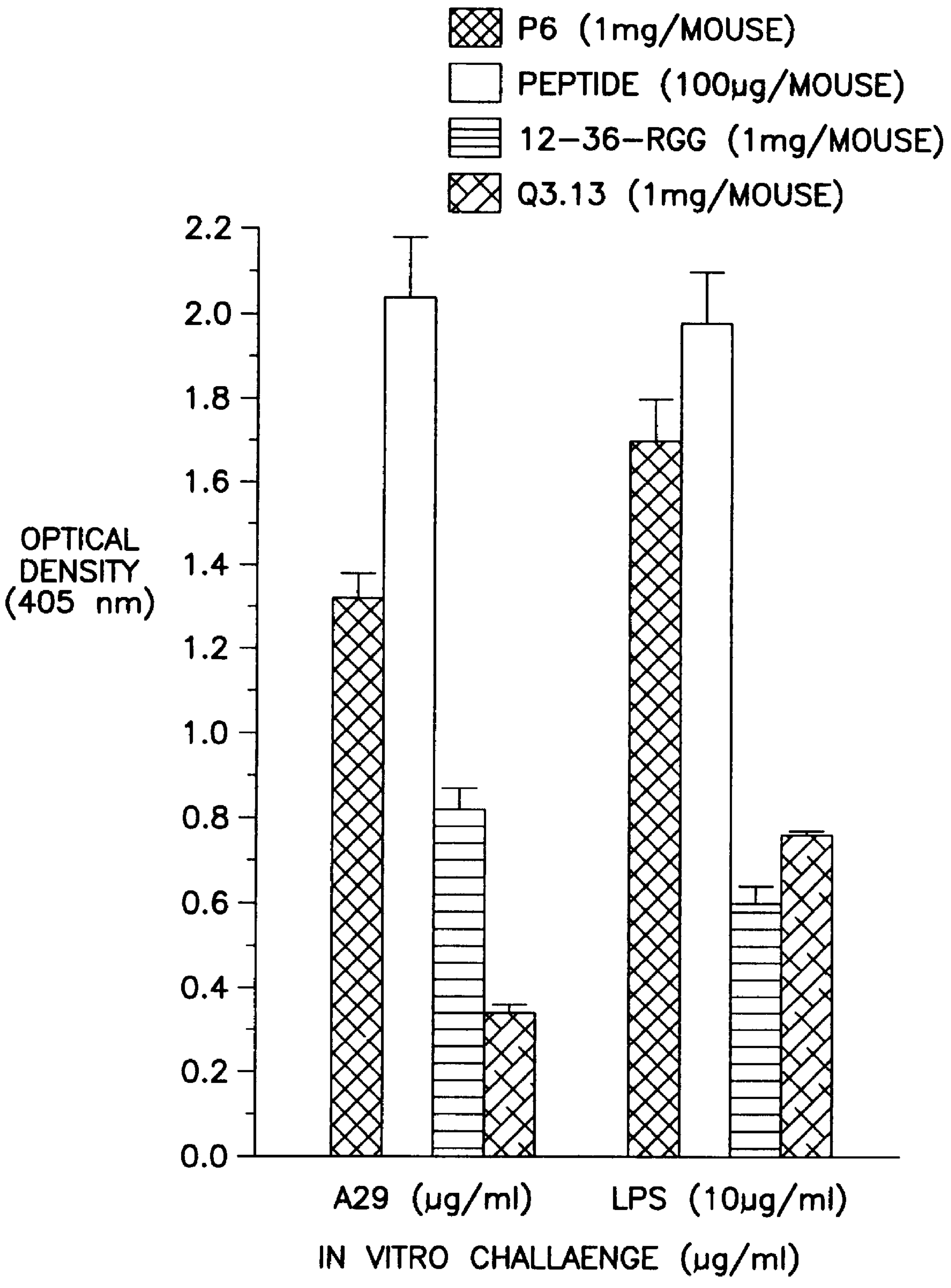
FIG. 5: In vivo tolerance induction with 12-26-IgG. Balb/c mice were injected with a tolerizing dose of control IgG (P6) at 1 mg/mouse [solid bars], the 12-26 peptide at 100 μg/mouse [open bar], the chemical conjugate of 12-26 chemically conjugated to rabbit gamma globulin (12-26-RGG) at 1 mg/mouse [stripped bar] and the fusion immunoglobulin (Q3.13) at 1 mg/mouse [dash-dot bar]. After 7 days, spleen cells were evaluated for responsiveness to in vitro challenge with an antigen containing the 12-26 epitope as described in FIG. 4.

The 12-26-IgG fusion proteins were tested for induction of tolerance in vivo. $CAF_1$ mice were injected with 1 mg of the 12-26-IgG fusion protein, 12-26-IgG or free peptide in saline. Control mice received PBS in saline. Spleen cells from these mice were challenged 10 days later with the 12-26-flagellin fusion protein in vitro. Responsiveness to the 12-26 was measured by ELISA assays at 4 days after challenge as described for FIG. 4. The results are shown in FIG. 5.

The results indicate the 12-26 IgG fusion proteins as well as the chemical conjugate (RGG-12-26) can induce tolerance in vivo and in vitro. See FIGS. 4 and 5.

EXAMPLE IV

Construction of Retroviral Vector Containing a DNA Sequence Coding for the 12-26 IgG1 Fusion Protein Several retroviral constructs have been prepared that are based on the murine Moloney leukemia retroviral vector MBAE, as described by Kang et al., *Proc. Natl. Acad. Sci.*, 87:9803 (1990)

The retroviral vector MBAE can be obtained from Dr. Hozumi or prepared as described by Kang et al., cited supra. Briefly, the retroviral vector containing the Moloney murine leukemia long terminal repeats and the neo gene coding for G418 resistance was modified by insertion of the β-actin promoter and enhancer sequences. The β-actin promoter and enhancer sequences were cloned downstream from the neo gene. Heterologous genes can then be inserted downstream from the β-actin promoter by subcloning with HindIII and SalI.

DNA sequences subcloned into MBAE were derived from PCR-amplified reverse transcribed RNA from transfectoma Q3 which contains the 12-26-IgG H chain. The Q3 transfectoma was prepared as described in Example II. The RNA from the Q3 transfectoma was harvested and incubated with reverse transcriptase in a standard PCR reaction as described in *Current Protocols in Molecular Biology*, cited supra. to form cDNA molecules. The cDNA molecules were amplified using the following primers:

$V_H$5' primer (SEQ ID NO:6):

5' TGG ACT AAG TCG ACA CCA TGG GAT GCA GC pep 3' primer (SEQ ID NO:7):

5' GGC AAC AGA AGC TTT CAC TTC TTC TTC TCG TAT 3'

One such cDNA includes a DNA sequence coding for the leader sequence and the 12-26 epitope from the variable heavy chain gene followed by a stop codon. The stop codon was designed into the PCR primer at the end of the DNA sequence coding for the last amino acid of 12-26 (in primer) to construct a peptide minigene.

Figure 7:
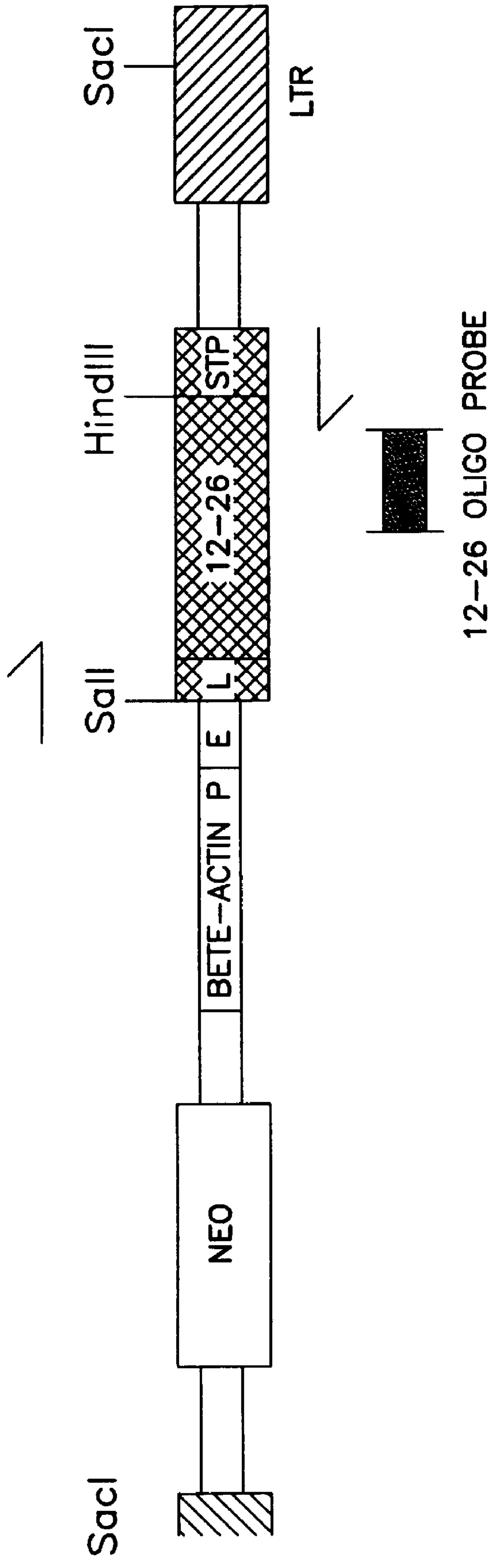
FIG. 7 shows construction of an MBAE retroviral vector containing the DNA sequence coding for the 12-26 epitope.

A DNA sequence coding for the leader sequence and the sequence coding for the 12-26 epitope followed by a stop codon was subcloned into pBluescript and sequenced and then subcloned into the MBAE vector. Subcloning was performed using SalI and HindIII to insert the peptide minigene downstream from the β-actin promoter and enhancer sequences, as shown in FIG. 7.

The recombinant MBAE vectors were transfected by lipofection into the ψ-2 cell line available from Dr. N. Hozumi (Toronto, Canada). The transfected cells lines were grown in RPMI 5% FCS in the presence of 0.8 mg/ml crude G418. G418 resistent clones were isolated by limiting dilution and viral titer was determined on NIH 3T3 cells in the presence of 0.8 mg/ml G418 (crude weight). For the peptide minigene construct, one transfected ψ-2 clone (MBAE pEP19) with a titer of $10^5$–$10^6$ CFU/ml was chosen for subsequent gene transfer experiments. Presence of helper virus was assayed using standard methods ("horizontal spread of infection" method), as described by *Current Protocols in Molecular Biology*, cited supra. and was not detected. Virus producing lines were thawed out fresh for each individual experiment.

Figure 6A:
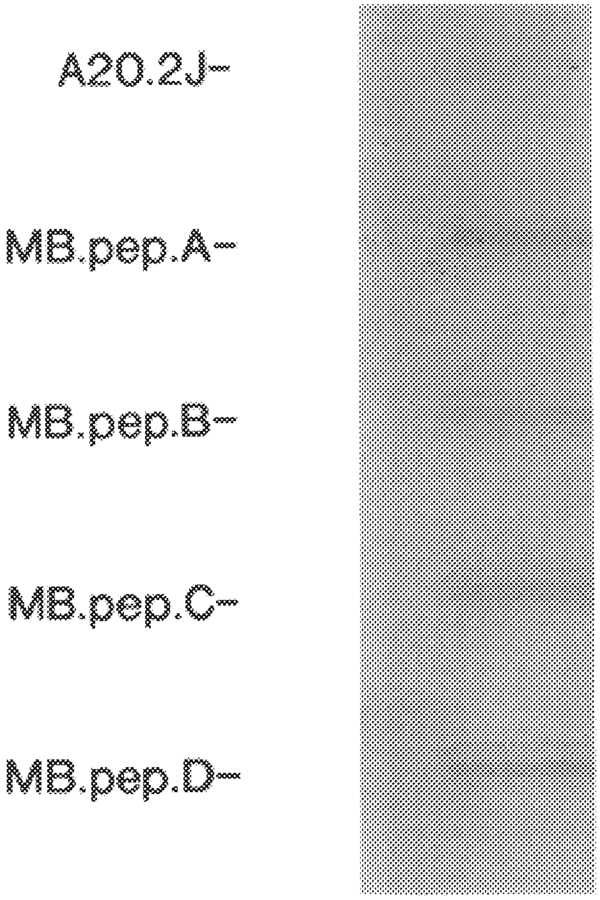
FIG. 6A: Western blot showing expression of the 12-26 peptide in supernatants from A20.2J cells infected with MBAE-12-26 vector. Supernatants were slot-blotted on nitro-cellulose and probed with anti-12-26 monoclonal antibody B3.11. MBpepA, MBpepB, MBpepC, and MBpepD represent individually infected A20.2J clones producing the 12-26 peptide coding for MBAE-12-26-vector.

An A20.2J B-cell lymphoma cell, available from ATCC, infected with the viral vector expressed and secreted the peptide as detected by Western blot. See FIG. 6A. After infection of A20.2J B-cell lymphoma cells, the cells were grown in G418 and 200 μl of supernatants were analyzed by Western blotting. Supernatants from four ψ-2/A20.2J clones infected with retroviral 12-26 minigene were slot blotted and reacted with monoclonal antibody B3.11 specific for the 12-26 epitope. As seen in FIG. 6A, the peptide was expressed in the infected lymphoma cells.

Figure 6B:
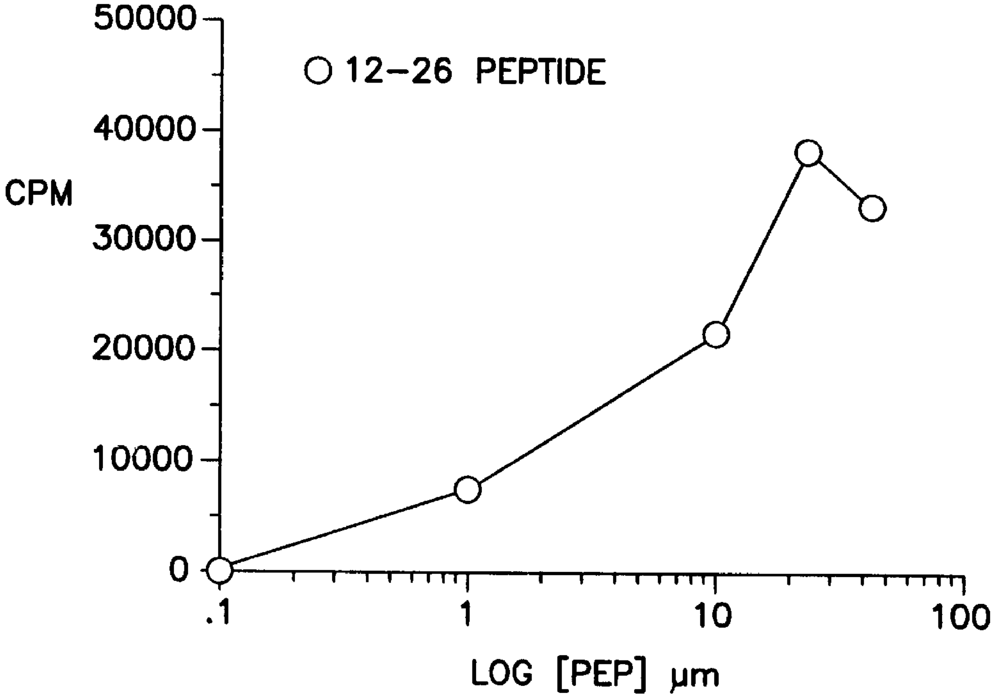
FIG. 6B and 6C show proliferation of a T-cell anti-12-26-IgG TH1 clone in response to incubation with supernatants from A20 cells infected with MBAE-12-26 vector or control supernatants.
Figure 6C:
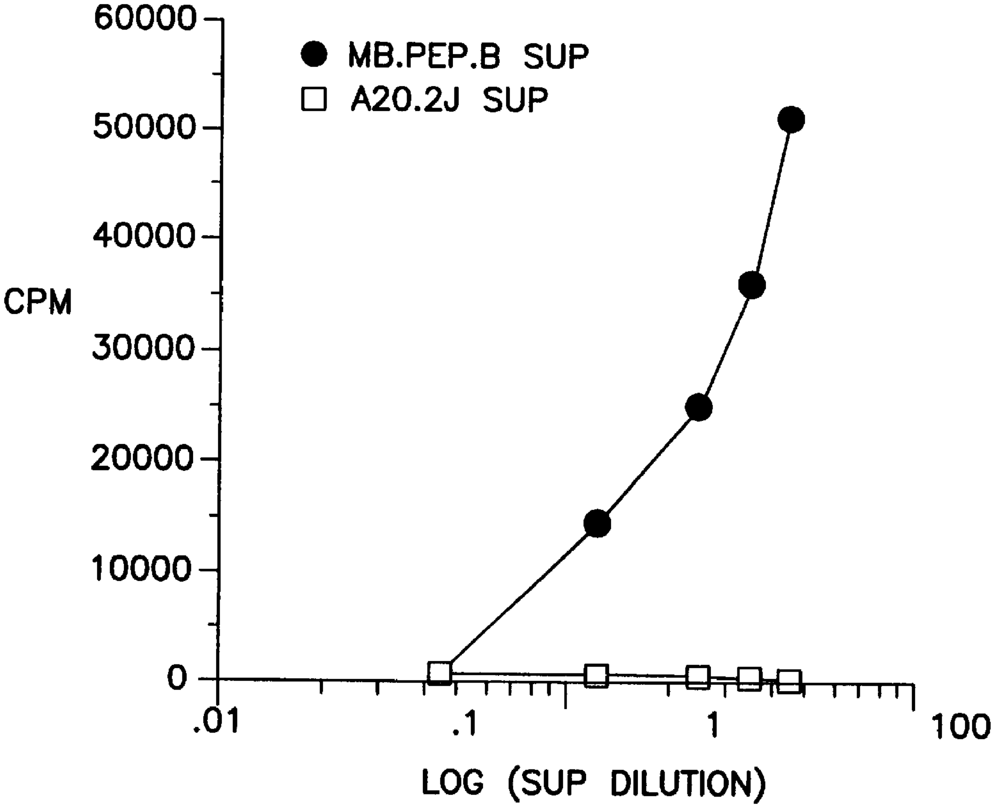

The A20.2J infected cells not only produce the peptide but also present it to a 12-26 reactive T-cell hybridoma. Briefly, titrated volumes of supernatants from infected A20.2J cells were incubated with a 12-26 reactive T-cell clones (T32) for 24–48 hours. The 12-26 reactive T-cell clones was obtained by Dr. Tom Briner and Dr. M. Gefter (Massachusetts Institute of Technology, Cambridge, Mass.). Responsiveness of the T-cell clone was measured by $^3$H-thymidine incorporation and standard IL-2 assay. The results are shown in FIG. 6B. The results indicate that A20 cells process this peptide so it can be presented to a 12-26 reactive T-cell clone. IL-2 production by these clones was also measured and the results show the 12-26 peptide is produced and secreted by the infected cells.

EXAMPLE V

Preparation of Mice Carrying Transfected Bone Marrow Cells

Mice carrying bone marrow cells transfected with the viral vector MBAE 12-26 coding for the 12-26 epitope (FIG. 7) were prepared. Bone marrow progenitors from Balb/c mice were infected with the MBAE 12-26 vector as described by Chambers et al., *Proc. Natl. Acad. Sci.*, 89:1026 (1992). Marrow donor Balb/c mice were pretreated intravenously with 150 mg/kg 5-fluorouracil for 3–4 days before marrow harvest. Fractionated marrow cells were kept on ice and then washed in complete RPM1 with 15% FC5 and 10 units/ml IL-3. The bone marrow cells were then cocultured with about an 80% confluent layer of irradiated (2000 rads) ψ-2 packaging lines. Co-culture with adherent ψ-2 virus producing line was done at 37° C. for 48 hours as follows:

5×$10^6$ marrow cells per 6 wells in 10 ml medium containing:
15% FCS
6 μg/ml polybrene
100 units/ml IL-6
200 units/ml IL-3

Nonadherent bone marrow cells were harvested after 48 hours, washed and resuspended in HEPES buffered Eaglis medium. Syngeneic recipient Balb/c mice were lethally irradiated with 900 rads and 4×$10^6$ cells in a volume of 400 μl were injected into the irradiated mice intravenously. Recipient mice were started on acidified water 1–2 weeks before transplantation to prevent gram negative infections and maintained in autoclaved microisolater cages with autoclaved food, bedding and acidified water supplemented with antibiotics.

Figure 8:
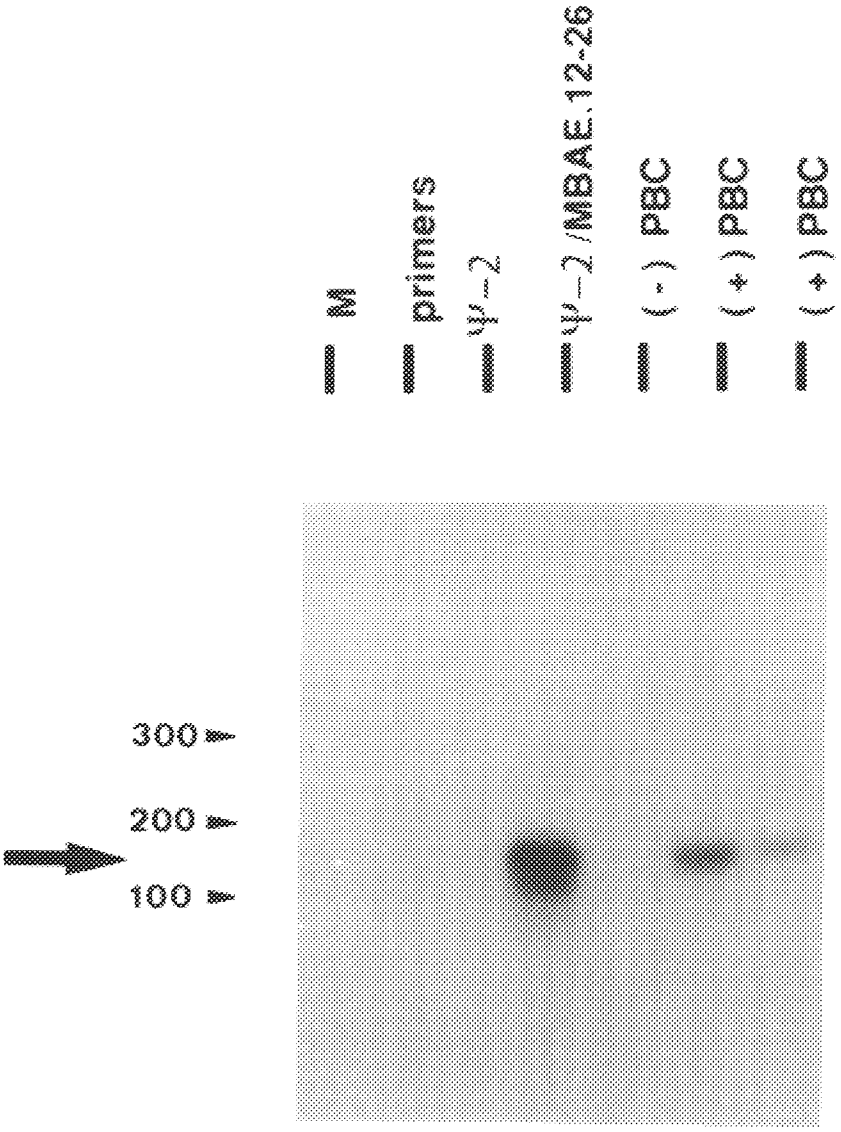
FIG. 8 shows a Southern blot of cDNA prepared from reverse transcribed polymerase chain reaction (PCR) products from MBAE-12-26 infected bone marrow cells after maturation in irradiated recipients. Peripheral blood cells were obtained from mice 2 weeks after receiving infected bone marrow cells. RNA was reverse-transcribed and PCR performed with $V_H$ and 12-26 primers. The gels were probed with an oligonucleotide probe complementary to the DNA sequence coding for the 12-26 epitope. The experiment demonstrates expression of mRNA coding for the 12-26 epitope based on RT-PCR of RNA from peripheral blood cells at 2 weeks after bone marrow transplantation.

After two weeks, the lymphoid cells from the recipient mice were harvested from tail bleeds and examined for the presence of the 12-26 sequence by RT-PCR. Fragments of about 100 base pairs were detected in both infected lymphoid cells and the ψ-2 MBAE 12-26 containing cell line. See FIG. 8.

Briefly, RNA from peripheral blood cells taken from the animals at 2 weeks or from infected Ψ-2 packaging lines was reverse transcribed. DNA sequences coding for the 12-26 epitope were amplified using the $V_H$ (SEQ ID NO:6) and pep (SEQ ID NO:7) primers. Amplified products were separated by agarose gel electrophoresis and products containing a DNA sequence coding for the 12-26 epitope were detected by Southern blot. The probe used to detect 12-26 coding sequences is as follows (SEQ ID NO:8):

5'- TGATCTACTG CAGCTGGAGG ACGCGCGGCG G - 3' Hybridization was conducted under standard conditions as described in *Current Protocols*, cited supra. A fragment detected in peripheral blood cells by hybridization to 12-26 probe indicated expression of the 12-26 epitope was occurring in the cells 2 weeks after administration.

What is claimed is:

1. A composition useful for inducing tolerance to one or more epitopes in a vertebrate animal, comprising:

(a) a tolerogenic amount of a fusion immunoglobulin produced from a vector DNA sequence encoding a fusion immunoglobulin heavy chain, light chain, or both heavy and light chains, said DNA sequence operably linked to functional transcriptional and translational control regions, which fusion immunoglobulin comprises one or more heterologous tolerogenic epitopes, to which the animal is being tolerized, fused to the variable region of said immunoglobulin heavy or light chain; and (b) a pharmaceutically acceptable excipient.

2. A composition according to claim 1, wherein the immunoglobulin is an isologous IgG.

3. A method for inducing and maintaining tolerance to one or more epitopes in a vertebrate animal, comprising:

(a) providing a vector that is stably maintained in cells which produce immunoglobulin, which vector comprises a DNA sequence encoding a fusion immunoglobulin heavy chain, light chain, or both heavy and light chains, operably linked to transcriptional and translational control regions functional in said cells, and which fusion immunoglobulin comprises one or more heterologous tolerogenic epitopes, to which said animal is being tolerized, fused to the variable region of said immunoglobulin heavy or light chain;

(b) stably transforming said cells, which are autologous to, or histocompatible with, said animal, with said vector to form transformed cells expressing said fusion immunoglobulin including said one or more epitopes; and (c) administering said transformed cells to said animal, wherein said transformed cells express said fusion immunoglobulin for the lifespan of said cells in said animal and thereby provide a persistent source of said one or more epitopes to maintain tolerance in said animals for at least the lifespan of said cells, thereby inducing and maintaining tolerance to said one or more epitopes.

4. A method according to claim 3, wherein said fusion immunoglobulin is a heavy chain dimer comprising two fusion immunoglobulin heavy chains.

5. A method according to claim 3, wherein said fusion immunoglobulin is a tetramer comprising two fusion immunoglobulin heavy chains and two light chains.

6. A method according to claim 1, wherein said one or more epitopes is fused to said immunoglobulin variable region at the N terminus of a framework region of said variable region.

7. A method according to claim 1, wherein said cells are hemopoietic cells or lymphoid cells.

8. A method according to claim 1, wherein (i) one or more of said tolerogenic epitopes is a peptide having the sequence SEQ ID NO:2; and (ii) said peptide is fused to the N terminus of the first framework region of said immunoglobulin variable region.

9. A method according to claim 1, wherein the vector is a retroviral vector.

10. A method according to claim 1, further comprising treating the animal to reduce the number of endogenous hemopoietic cells before administering said transformed cells.

11. A method for inducing tolerance to one or more epitopes in a vertebrate animal, comprising administering to said animal an effective tolerogenic amount of a fusion immunoglobulin which comprises an immunoglobulin heavy chain, light chain or both heavy and light chains to which is fused, at the N-terminus of a framework region of said chain, one or more heterologous tolerogenic epitopes to which tolerance is being induced, thereby inducing said tolerance.

12. A method according to claim 11, wherein said epitope is fused to the N-terminus of the first framework region of the immunoglobulin heavy chain.

13. A method for inducing and maintaining tolerance to one or more selected epitopes in a vertebrate animal, comprising:

(a) for inducing tolerance, administering to said animal a pharmaceutical composition which comprises (i) a tolerogenic amount of a fusion immunoglobulin having said one or more epitopes fused to the immunoglobulin heavy chain variable region, light chain variable region or both the heavy chain and the light chain variable regions; and (ii) a pharmaceutically acceptable excipient, and (b) administering to said animal transformed autologous or histocompatible cells producing said fusion immunoglobulin in numbers sufficient to maintain tolerance to said one or more epitopes, which cells stably express DNA encoding said fusion immunoglobulin chain operably linked to transcriptional and translational control sequences functional in said cells, wherein the DNA is expressed in said animals for the lifespan of said administered transformed cells, thereby providing a persistent source of said one or more epitopes to maintain tolerance in said animals for at least the lifespan of said cells, thereby inducing and maintaining said tolerance.

14. A method according to claim 13, wherein said one or more epitope is fused to said immunoglobulin variable region at the N terminus of a framework region of said variable region.

15. A method according to claim 13, wherein said one or more epitope is fused to the immunoglobulin heavy chain.

16. A method according to claim 13, wherein said one or more epitope is fused to the immunoglobulin light chain.

17. A method according to claim 13, wherein said cells are hemopoietic or lymphoid cells.

18. A method according to claim 6 or 14 wherein said epitope is fused to the first framework region of said immunoglobulin variable region.

19. A method according to claim 18, wherein said epitope is fused to the immunoglobulin heavy chain.

20. A method according to claim 17, wherein said cells are hemopoietic or lymphoid cells.

21. A method for inducing and maintaining tolerance to one or more selected epitopes in a vertebrate animal, comprising administering to said animal transformed autologous or histocompatible cells which stably produce fusion immunoglobulin molecules having said one or more epitopes fused to an immunoglobulin heavy chain, light chain or both, wherein said administered cells produce said fusion immunoglobulin for the lifespan of said cells in said animal and thereby provide a persistent source of said one or more epitopes to maintain tolerance for at least the lifespan of said cells in said animal, thereby inducing and maintaining said tolerance.

22. A method according to claim 3, wherein said animal is a mammal.

23. A method according to claim 11, wherein said animal is a mammal.

24. A method according to claim 13, wherein said animal is a mammal.

25. A method according to claim 21, wherein said animal is a mammal.

26. A composition according to claim 1, wherein said one or more epitopes is fused to said immunoglobulin variable region at the N-terminus of a framework region of said variable region.

27. A composition according to claim 26, wherein said framework region is the first framework region of said variable region.

28. A composition according to claim 27, wherein said framework region is the first framework region of said variable region of the immunoglobulin heavy chain.

* * * * *

UNITED STATES PATENT AND TRADEMARK OFFICE

CERTIFICATE OF CORRECTION

PATENT NO. : 5,817,308 Page 1 of 1
DATED : October 6, 1998
INVENTOR(S) : David W. Scott and Elias T. Zambidis It is certified that error appears in the above-identified patent and that said Letters Patent is hereby corrected as shown below:

Column 26,
Lines 59, 63 and 65, please delete "1" and insert -- 3 --;

Column 27,
Lines 4 and 6, please delete "1" and insert -- 3 --; and

Column 28,
Line 13, please delete "17" and insert 18 --.

Signed and Sealed this

Tenth Day of February, 2004

JON W. DUDAS
*Acting Director of the United States Patent and Trademark Office*